United States Patent [19]

Morgan et al.

[11] Patent Number: 5,420,427
[45] Date of Patent: May 30, 1995

[54] MOBILE, MULTI-MODE APPARATUS AND METHOD FOR NONDESTRUCTIVELY INSPECTING COMPONENTS OF AN OPERATING SYSTEM

[75] Inventors: Ira L. Morgan; Robert H. Rice; Joseph E. Bolger; Robert M. Crane, all of Austin, Tex.

[73] Assignee: Integrated Diagnostic Measurement Corporation, Austin, Tex.

[21] Appl. No.: 982,381

[22] Filed: Nov. 25, 1992

Related U.S. Application Data

[63] Continuation-in-part of Ser. No. 541,981, Jun. 22, 1990, abandoned.

[51] Int. Cl.⁶ .............................................. G01N 23/18
[52] U.S. Cl. .............................. 250/360.1; 250/358.1; 378/59
[58] Field of Search .............. 378/59; 250/358.1, 360.1

[56] References Cited

U.S. PATENT DOCUMENTS

| | | | |
|---|---|---|---|
| 3,023,312 | 2/1962 | Wood | 250/360 |
| 3,066,254 | 11/1962 | Price et al. | 250/498.1 |
| 3,088,027 | 4/1963 | Graham . | |
| 3,108,186 | 10/1963 | Flavell . | |
| 3,445,655 | 5/1969 | Curry | 250/258.1 |
| 3,521,059 | 7/1970 | Stolle | 378/59 |
| 4,352,065 | 9/1982 | Rogachev et al. | 324/238 |
| 4,415,980 | 11/1983 | Buchanan | 378/58 |
| 4,425,505 | 1/1984 | Jones et al. | 250/359.1 |
| 4,467,654 | 8/1984 | Murakami et al. | 73/640 |
| 4,600,998 | 7/1986 | Huet | 364/507 |
| 4,680,470 | 7/1987 | Heald | 250/358.1 |
| 4,725,963 | 2/1988 | Taylor et al. | 364/507 |
| 4,928,283 | 5/1990 | Gordon | 378/20 |
| 5,138,644 | 8/1992 | McArdle et al. | 378/55 |

FOREIGN PATENT DOCUMENTS

| | | |
|---|---|---|
| 0201849 | 11/1986 | European Pat. Off. . |
| 0304708 | 3/1989 | European Pat. Off. . |
| 3818542 | 12/1989 | Germany ................................ 378/59 |
| 58-117445 | 7/1983 | Japan . |
| 2211708 | 5/1989 | United Kingdom ................... 378/58 |

OTHER PUBLICATIONS

AS&E CT Scanner Marketing Information pp. 1–13.
Anon. "Invasion of the Body Scanners," *Technology Illustrated* p. 67.

*Primary Examiner*—Constantine Hannaher
*Attorney, Agent, or Firm*—Jerry M. Keys; Heinz D. Grether

[57] ABSTRACT

A mobile apparatus for and a method of non-contacting, nondestructive, on-line inspection of installed components of plants, facilities or other systems. The apparatus and method use penetrating radiation sources and detectors mounted on a ring assembly which can be placed about vertical or horizontal components while they remain in place and in use. The ring assembly is held in place by a yoke assembly in a manner that allows the ring to be rotated relative to the yoke assembly so that multiple scans of the same component cross-section can be performed from different angles. The apparatus is also capable of sub-positioning the detectors relative to the source while the ring assembly is stationary to increase the number of scans that can be taken from different angles. The yoke assembly, in turn, is mounted on a beam assembly in a manner that allows the yoke assembly to move relative to the beam assembly. The apparatus can operate in multiple scanning modes and the resulting data collected can be processed using both application-specific, real-time data analysis techniques and available computerized axial tomographic (CAT) scanning data processing algorithms and techniques.

9 Claims, 23 Drawing Sheets

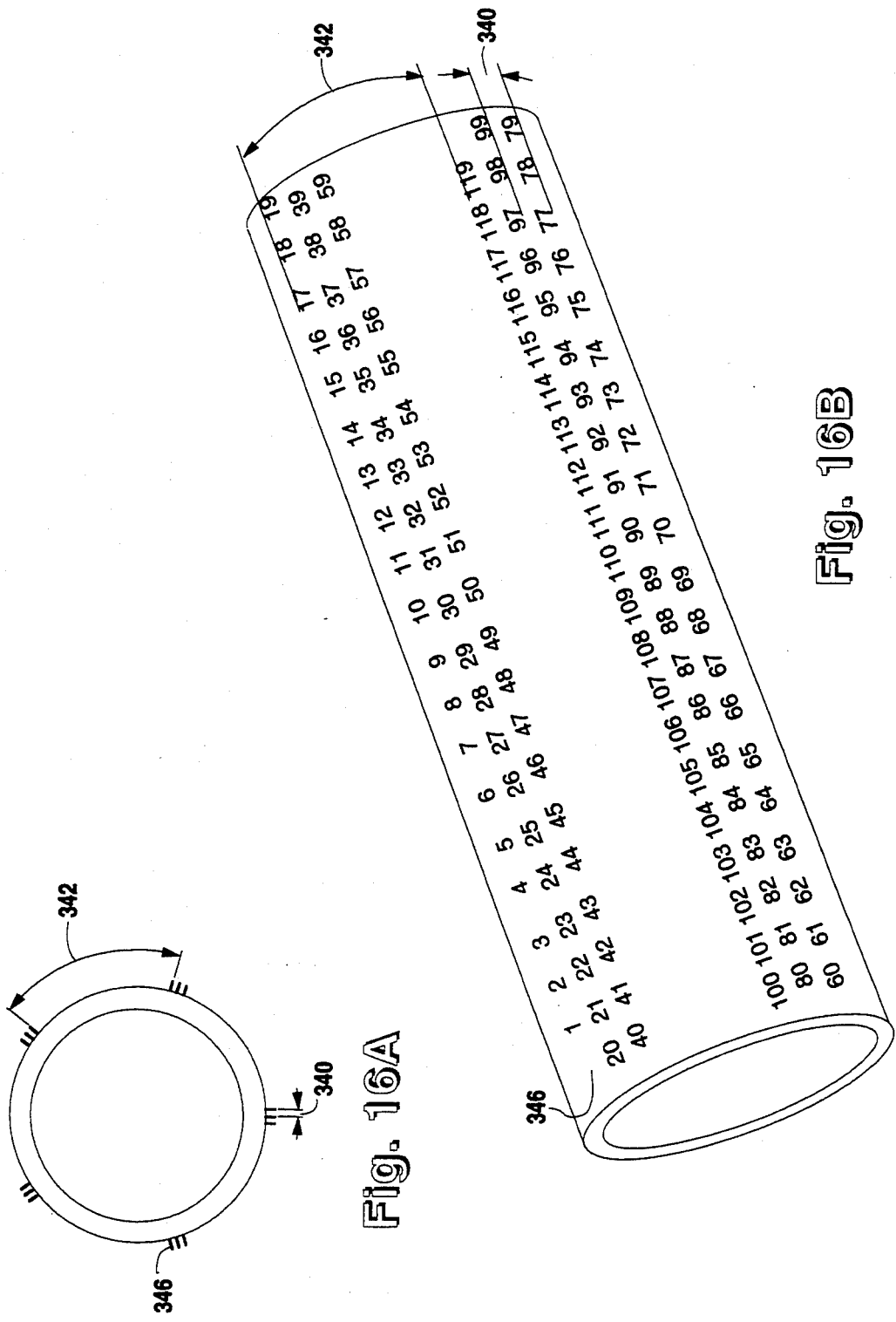

MOBILE, MULTI-MODE APPARATUS AND METHOD FOR NONDESTRUCTIVELY INSPECTING COMPONENTS OF AN OPERATING SYSTEM

CROSS-REFERENCE TO RELATED APPLICATION

This application is a continuation-in-part patent application from U.S. patent application Ser. No. 07/541,981, filed Jun. 22, 1990, entitled "A Mobile, Multi-Mode Apparatus and Method for Nondestructively Inspecting Components of an Operating System," now abandoned.

FIELD OF THE INVENTION

The present invention relates generally to a method of and apparatus for non-contact, nondestructive inspection of objects using penetrating radiation and, in particular, relates to a mobile scanning apparatus and method for nondestructive measurements and inspection of stationary components, such as piping, elbows, pumps and defuzers of an operating facility, plant or system while the components are in use for the purpose of determining use degradation.

BACKGROUND OF THE INVENTION

In the past, many attempts have been made to develop methods of nondestructive inspection of structural or tubular fluid transmission components of plants and facilities, as exemplified by U.S. Pat. Nos. 4,415,980 and 4,425,505. Many of these inspection methods required that the facility be shut down and at least partially disassembled in order to obtain useful data. Nevertheless some prior art methods attempted to perform nondestructive testing on such components while the components were in use, such as U.S. Pat. Nos. 3,006,251; 4,352,065; 4,467,654; and 4,680,470. Of these, U.S. Pat. Nos. 3,006,251 and 4,680,470, disclose use of penetrating radiation.

U.S. Pat. No. 3,006,251, discloses a device that scans pipe, using both penetrating radiation and electromagnetic fields, while being translated along the length of oil and gas field pipes. However the disclosed device has serious disadvantages. The scanning was not performed in a non-contacting manner and, therefore, was inoperable on hot insulated pipe. The device was also dependent on maintaining a concentric position around the pipe so that the radiation gauge would not be off center. The radiation gauge also gave only one thickness measurement rather that complete multi-angle and cross-sectional measurements. No method is disclosed for monitoring the position of the gauge either longitudinally or rotationally about the object as it scanned the pipe.

Additionally, the disclosed device could not be opened and closed about the pipe under examination, thereby virtually requiring that the system would have to be shut down and partially disassembled in order to position the device about in-place pipe to begin its inspection.

U.S. Pat. No. 4,680,470, discloses another prior art apparatus and method which uses penetrating radiation to detect flaws in installed objects. However, the disclosed method was passive in that it relied on background radiation for the radiation source, thereby restricting its use to detecting major defects or flaws. In particular, the primary system disclosed is only operable on objects that contain radiation sources inside the object. An alternative system is disclosed where a radioactive liquid is placed on the outer surface of the object, however the usefulness of this method is limited to showing flaws on the outer surface of the object and is impracticable to use in non-nuclear facilities due to safety and public health concerns. Since the strength of the radiation is unknown, the system is only capable of detecting flaws such as cracks and pits which manifest immediate changes in a localized area. More gradual flaws are much more difficult to detect with a passive system. Additionally, the disclosed system only contemplates translating the disclosed radiation detector along the length of a pipe but fails to disclose any particular means for accomplishing such movement.

SUMMARY OF THE INVENTION

Briefly, the present invention provides a new method of and mobile apparatus for, nondestructively inspecting installed stationary objects or components, such as insulated and non-insulated piping, pumps, elbows and defuzers of a facility regardless of whether the component is oriented vertically, horizontally or at an angle between vertical and horizontal.

The mobile apparatus comprises a scanning unit have a ring assembly for encircling the component to be scanned, a beam, a yoke assembly positioned on the beam for supporting the ring assembly about the component wherein the yoke assembly is movable relative to the beam. A penetrating radiation source for transmitting radiation through the component and a detector array for detecting the transmitted radiation are mounted opposite each other on the ring assembly. Stepping motors mounted on the yoke assembly are used to rotate the ring assembly relative to the yoke assembly about the component to obtain multiple scans of a cross-section of the component. Motors mounted on the beam are used to translate the yoke assembly relative to the beam assembly along the length of the component to be scanned. The operator transmits predetermined signals stored in a computer to control the motors.

An encoder on the beam motor monitors the longitudinal position of the ring and yoke assembly relative to the beam assembly and an encoder on the yoke motor is used to monitor the rotational position of the ring assembly relative to the yoke assembly. The position monitors are used to accurately determine the position of the portion of the component under examination. A data processing system sends control signals to the apparatus for controlling the translational and rotational movements of the source and detector, receives position signals from the monitors and receives signals from the detector array. The apparatus may be operated in a gauging mode and/or an analytical mode. During the gauging mode, the apparatus initially scans a limited number of cross-sections of a component along the longitudinal length of the component at a limited number of rotational positions. The data processing system uses a limited-angle collection and analysis method to determine the dimensions of the component and to locate flaws which need further investigation. During the analytical mode, the apparatus scans at least one cross-section of the component at the location of the previously detected flaw at a larger number of rotational positions. The data processing means is programmed with computer tomographic methods to analyze the resulting signals generated during each scan to reconstruct image of the detected flaw in order to better identify the characteristics of the flaw.

BRIEF DESCRIPTION OF THE DRAWINGS

FIGS. 16A and B are illustrative drawings of a scanning pattern along a section of pipe used by the present invention in a gauging mode.

DESCRIPTION OF THE PREFERRED EMBODIMENT

Figure 1A:
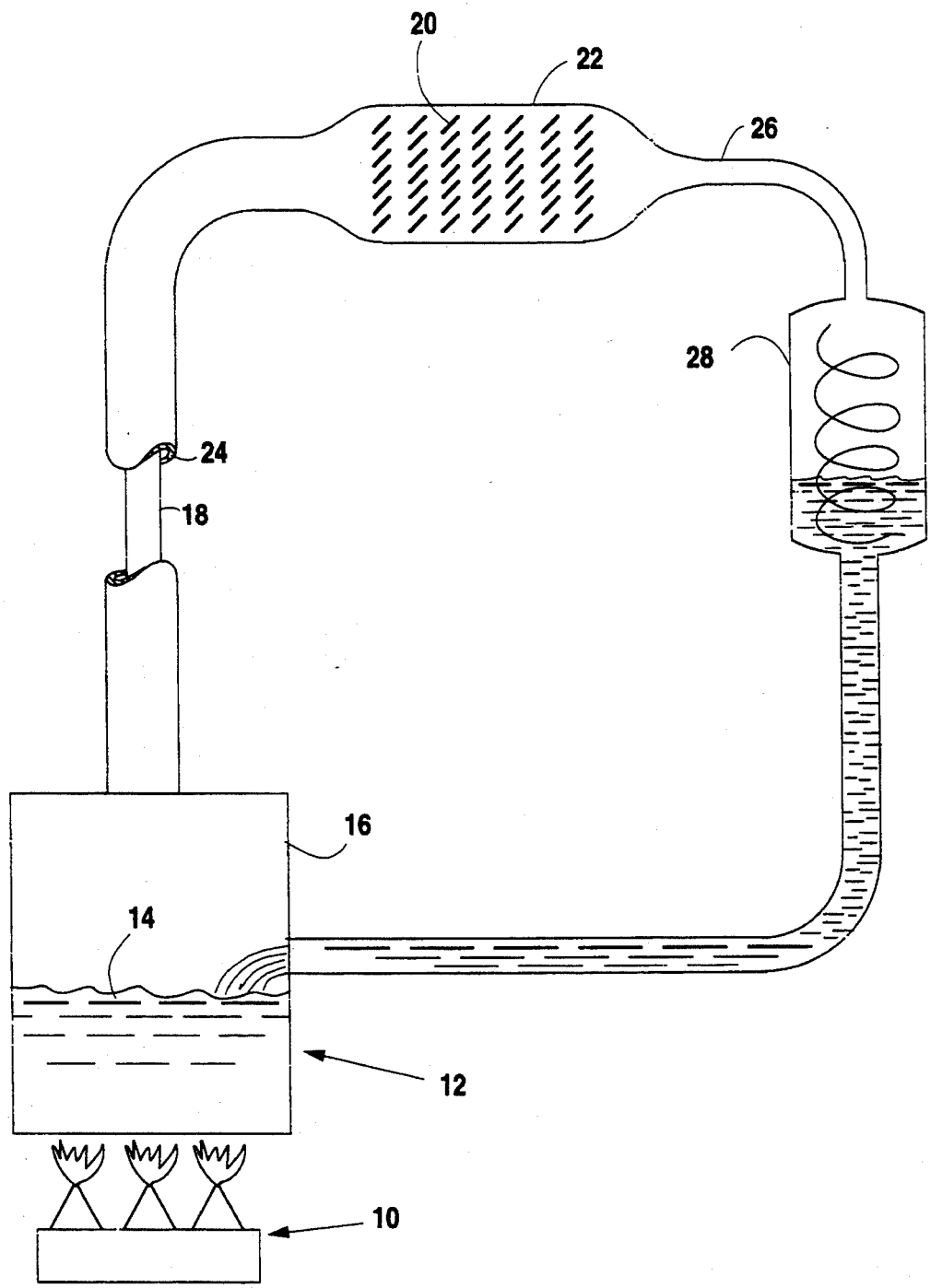
FIG. 1A is a simplified diagrammatic illustration of a steam power generating facility showing vertically and horizontally-oriented components on which the present invention may be employed.

FIG. 1A is a diagrammatic illustration of a typical steam powered electrical generating facility to which the present invention is well suited for inspection purposes. An energy source 10 generates heat which heats the boiler 12. As the water 14 in the boiler 12 begins to boil it lets off steam 16. The steam 16 travels through steam pipe 18 to the turbines 20 of an electrical power generator 22. The steam pipe 18 is covered by a sheath of insulating material 24 to prevent energy losses. The steam that is exhausted 26 from the generator 22 passes through a condenser 28 which condenses the steam into water. The condensed water then returns to the boiler 12 for another cycle.

Figure 1B:
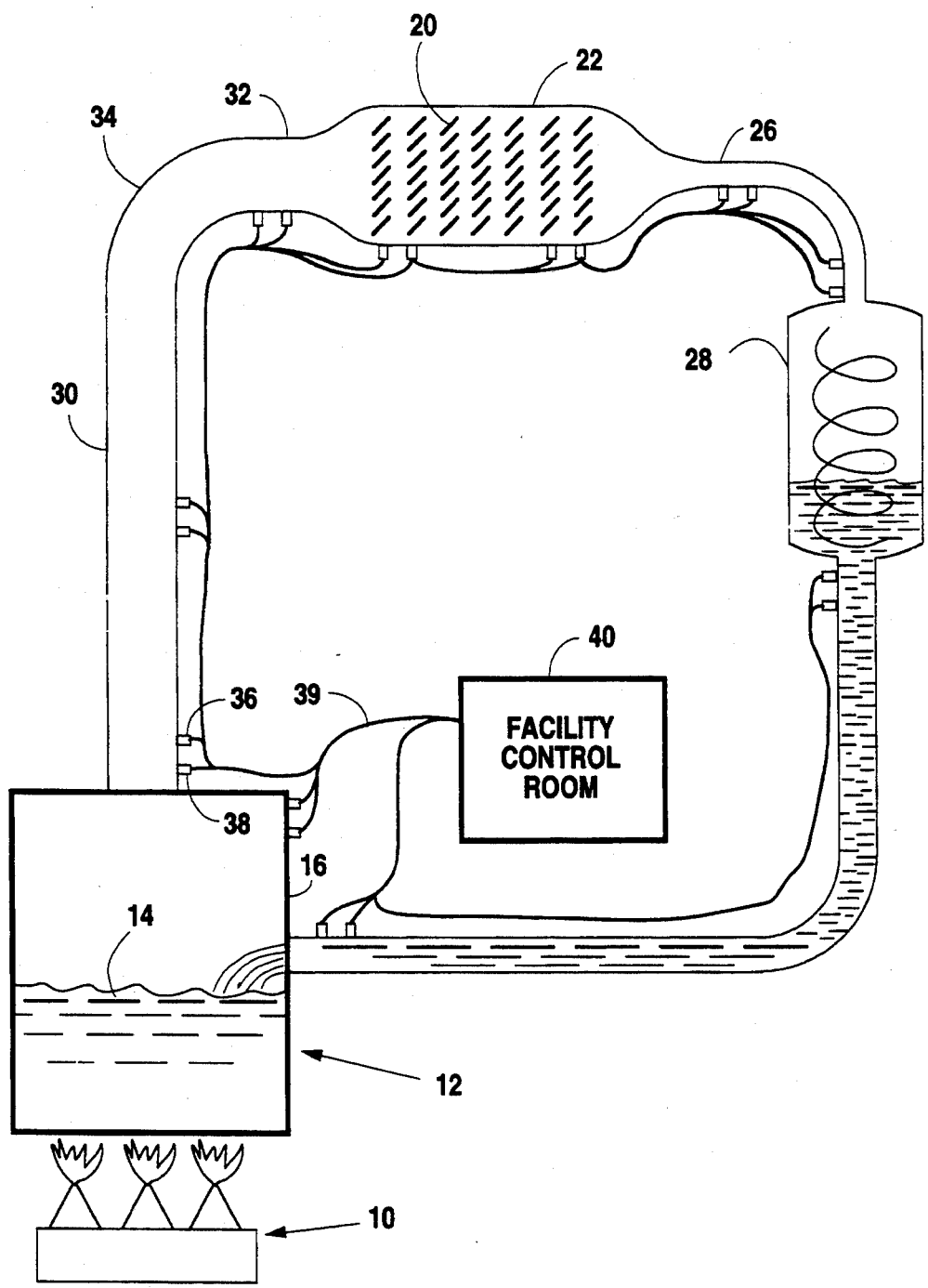
FIG. 1B is a simplified diagrammatic illustration of a steam power generating facility showing temperature and pressure sensors at increments along the steam line.

As shown in FIGS. 1A and 1B, a typical power generating facility includes both vertically-oriented components 30 and horizontally-oriented components 32. In addition, a typical facility includes components 34 whose orientation may be at virtually any angle between vertical and horizontal. FIG. 1B also shows, by diagrammatic illustration, conventional temperature sensors 36 and pressure sensors 38 in a typical steam powered electrical generating facility. The information collected by these sensors 36 & 38 is typically sent to a computer in the facility control room. However, the information can also be collected by the data collection system 64 of the present invention. Since the positions of the sensors are known, the temperature and pressure at any point along the steam line can be extrapolated.

Furthermore, two (2) types of temperature sensors are typically already used at each sensor location. One type of temperature sensor measures the temperature of the outside of the pipe. The other type of sensor (not shown) is mounted inside the pipe, typically a thermocouple, measures the temperature of the fluid or gas inside the pipe. With these measurements it is possible to extrapolate the temperature at any point within the pipe and pipe wall.

The apparatus (FIG. 2) and method of the present invention is ideally suited to inspect steam pipe 18 and other components in such electric power plants while such pipe or other components are in place and in use. In order to perform such inspections using the apparatus it is not necessary to disassemble the steam pipe 18 into sections, to shut down the facility, or remove insulation 24. However, the inspection apparatus must be capable of inspecting the facilities components as it finds them; whether they are oriented vertically, horizontally, at some angle between vertical and horizontal, or through insulation or other opaque obstructions which may be encountered.

The use of the present invention is not limited to steam transportation systems in steam-driven, electrical power generation facilities. The invention is also useful in chemical plants and refineries or in any facility or structural system utilizing installed components about which the Apparatus can be positioned and are made of materials that can be scanned by penetrating radiation. The preferred embodiment disclosed herein, however, is particularly adapted to inspecting steam pipe in a steam-driven, electrical power generating facility.

Figure 2:
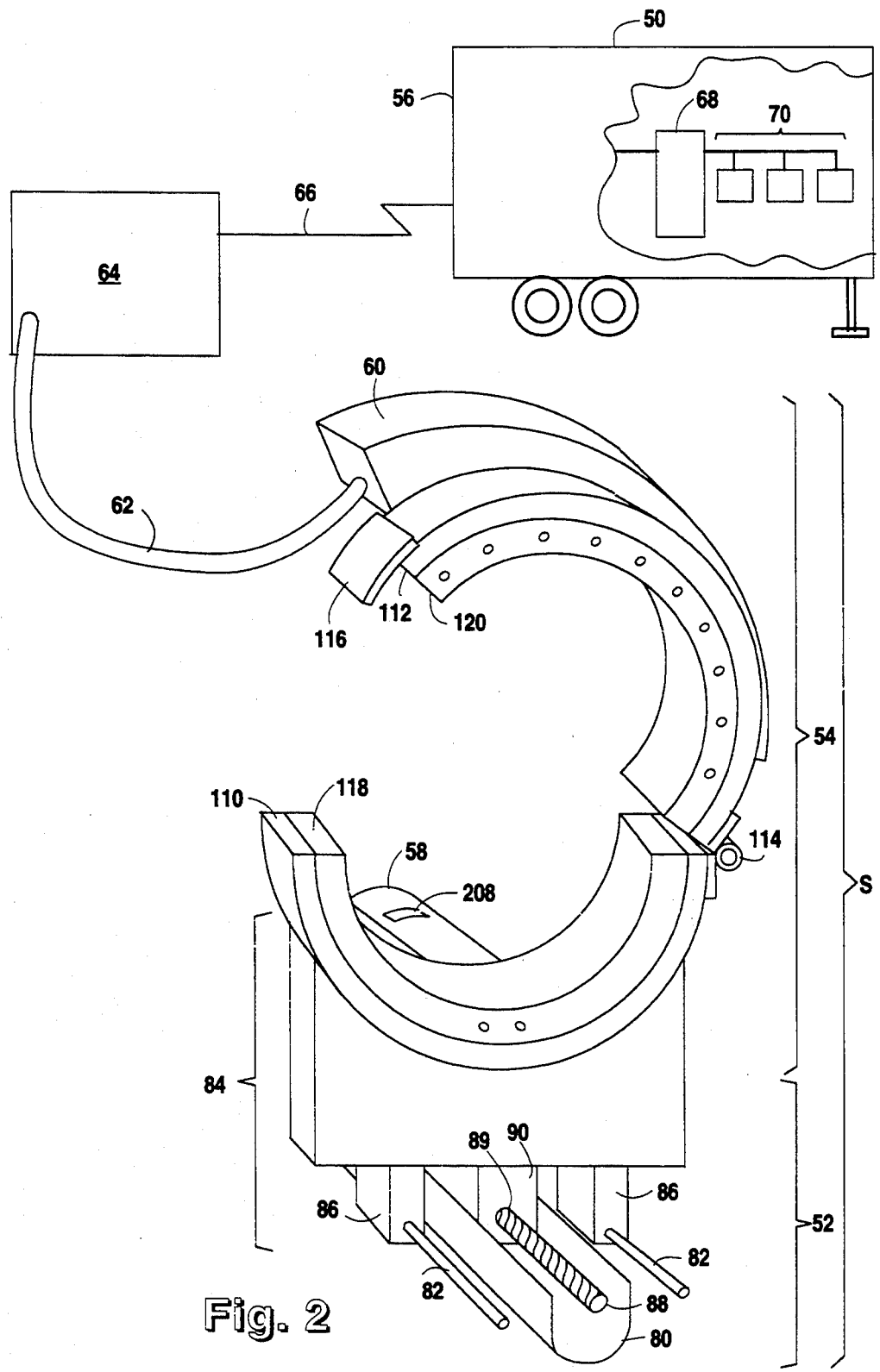
FIG. 2 is an illustrative drawing of the overall apparatus of the present invention.

FIG. 2 is a diagrammatic illustration of the mobile apparatus embodying the invention which has been particularly adapted to inspect pipe in steam-driven, electrical power plants. The apparatus is transported to the power plant in a trailer 50. The scanning Unit S and data collection subsystem 64 are taken out of the trailer 56 and the scanning unit S positioned about the pipe 18 to be inspected. The scanning unit S includes a gantry 52 and a ring assembly 54. The gantry system 52 includes a beam 80, one or more linear rod and ball bearing arrangements 86, a threaded rod and bearing arrangement 89 and an actuation system shown in FIG. 3 and described below, is placed parallel to the axis of pipe 18 so that once in place the ring assembly 54 will fit around the pipe 18 and can travel along the length of the pipe 18. The ring assembly 54 is composed of two inner ring halves 118 and 120 and two outer ring halves 110 and 112.

A penetrating radiation source 58 is mounted on one half of the inner ring 118. Mounted onto the other side of the ring assembly 54 on the other inner ring half 120 is the detector array housing 60. It is mounted to face the radiation source 58. While the source 58 and detector array housing 60 are translated along and rotated about the steam pipe 18, the source 58 emits gamma or x-ray penetrating radiation in the direction of the detector array housing 60. The presence of pipe 18 between the source 58 and detector array housing 60 causes the radiation to be attenuated. The attenuated radiation is converted into electrical signals within the detector array housing 60 as described below. The electrical signals generated within the detector array housing 60 are transmitted through wiring in the umbilical cord 62 to a data collection subsystem 64. The subsystem 64 collects the signals transmitted from the detector array housing 60 and prepares them for transmission to the remote trailer via a fiber optic transmission system 66 or other suitable transmission system. The signals transmitted by the fiber optic transmission system is received by the main computer 68 and its peripherals 70 in the trailer. The data collection, preparation, transmission, and processing is described in greater detail below.

GANTRY SYSTEM

Figure 3:
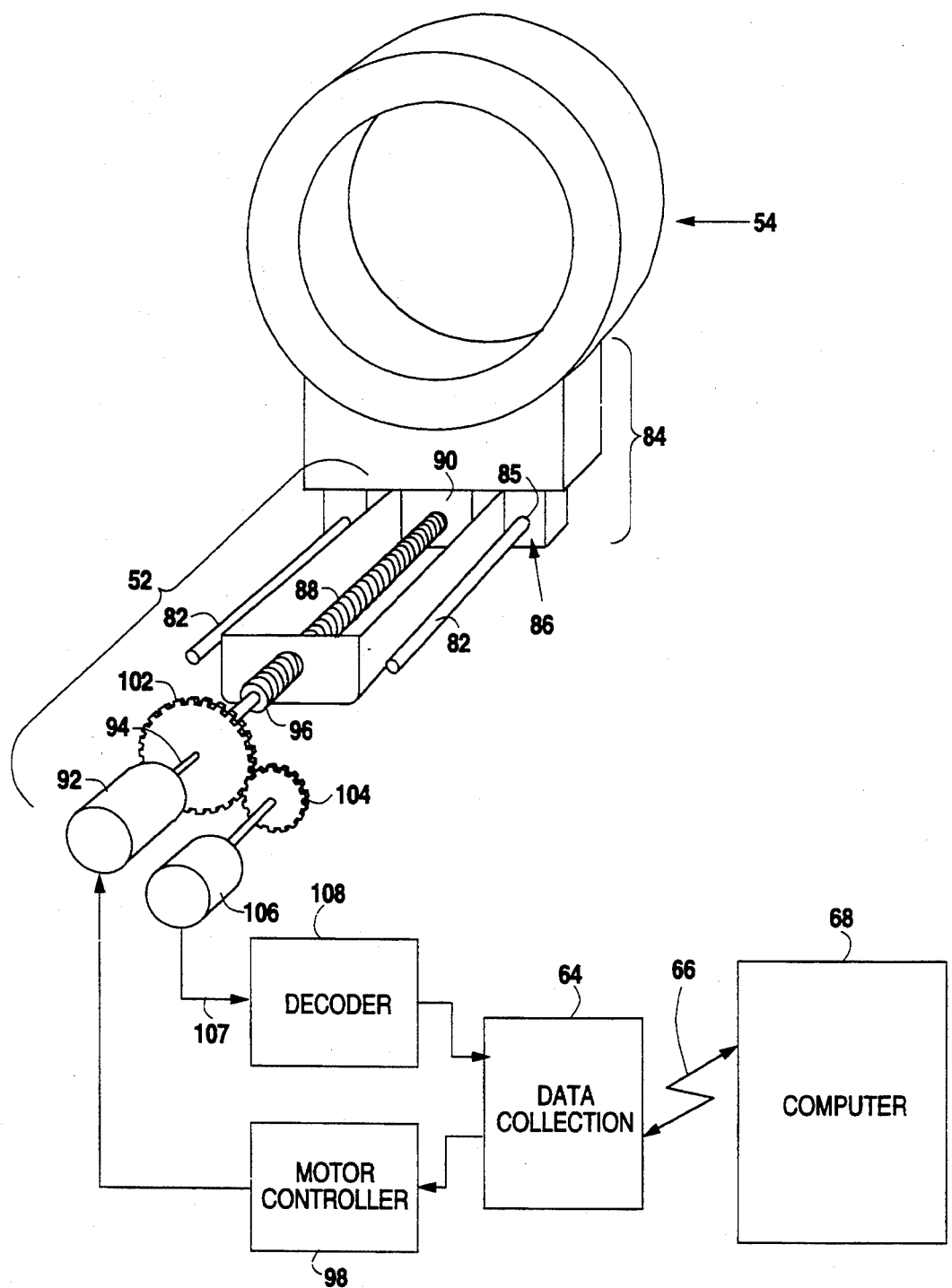
FIG. 3 is an illustrative drawing of the gantry system of the present invention with emphasis on the longitudinal translation components

FIG. 3 is an illustrative drawing of the gantry system 52. The gantry system 52 is built around a beam 80. Although the figure shows a C-shaped beam, other structures may also be used. Mounted to the sides of the beam 80 are smooth rods 82. The yoke assembly 84 is connected to the smooth rods 82 mounted to the outside of the beam 80 by ball bearings 85, creating a linear rod and ball bearing arrangement 86. The linear rod and ball bearing arrangement 86 allows the yoke assembly 84 to travel along the length of the beam 80 with ease.

A threaded rod 88 is mounted within the C-shaped beam 80 in such a manner that it can be rotated while it is held in place. The threaded rod 88 is also fitted into a female threaded coupling 90 which is mounted on the yoke assembly 84. In this manner when the threaded rod 88 is rotated the yoke assembly 84 is translated along the length of the beam 80. The direction of translation is determined by the direction in which the threaded rod 88 is rotated.

The threaded rod 88 is rotated with an electrical motor 92. The shaft 94 of the electrical motor 92 is connected to the threaded rod 88 via the shaft 94. A motor controller 98 conditions control signals it receives from the computer system 68 via the fiber optic cable 66, data collection subsystem 64, and umbilical cord 62.

FIG. 3 also shows how the translational position of the yoke assembly 84 is monitored. Since the position of the yoke assembly 84 is directly dependant on the rotation of the threaded rod 88, the present invention monitors the position of the yoke 84 by optically encoding the rotation of the threaded rod 88. Gears 102 and 104 are mounted to the shaft 94 of the motor 92 and optical encoder 106. Thereby as the threaded rod 88 rotates the gear 102 and 104 also rotate and optical encoder 106 monitors this rotation. The manner in which the rotation is encoded is described in greater detail below.

YOKE AND RING ASSEMBLY

Figure 4A:
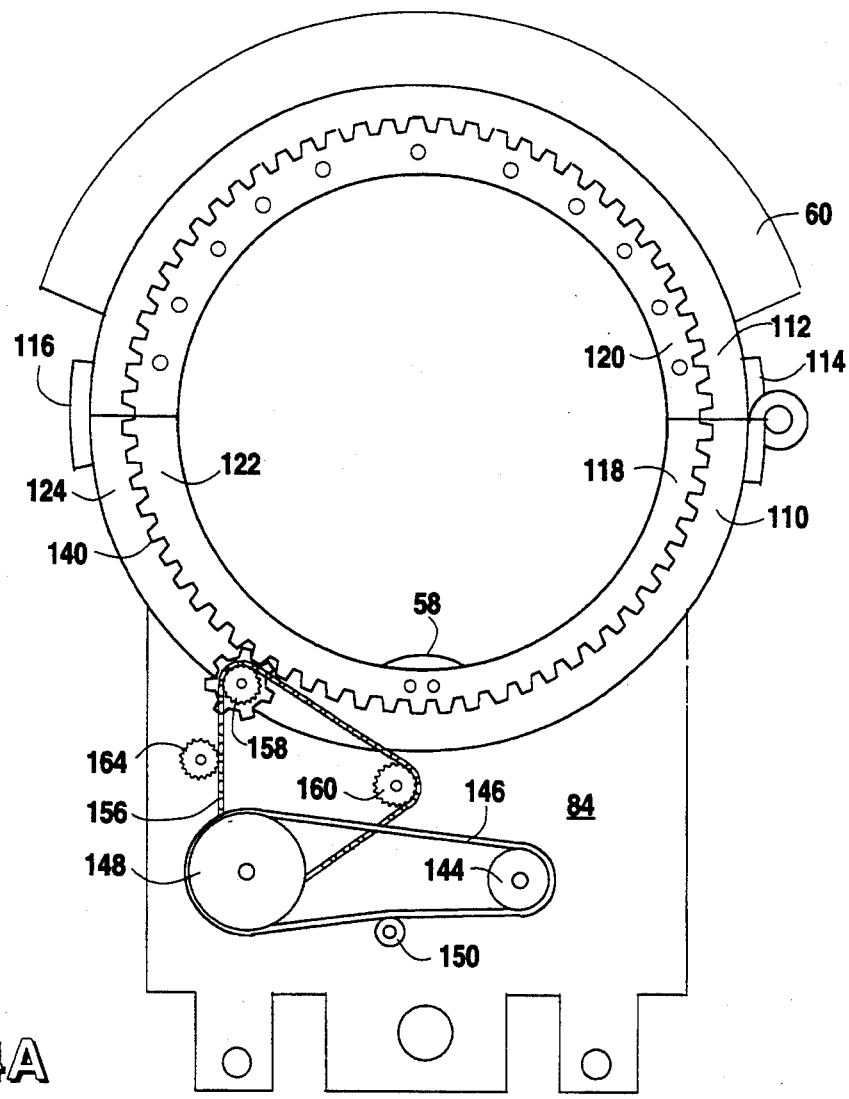
FIG. 4A is an illustrative drawing of the yoke and ring assembly components of the gantry system of the present invention with emphasis on the rotational translation components.
Figure 4B:
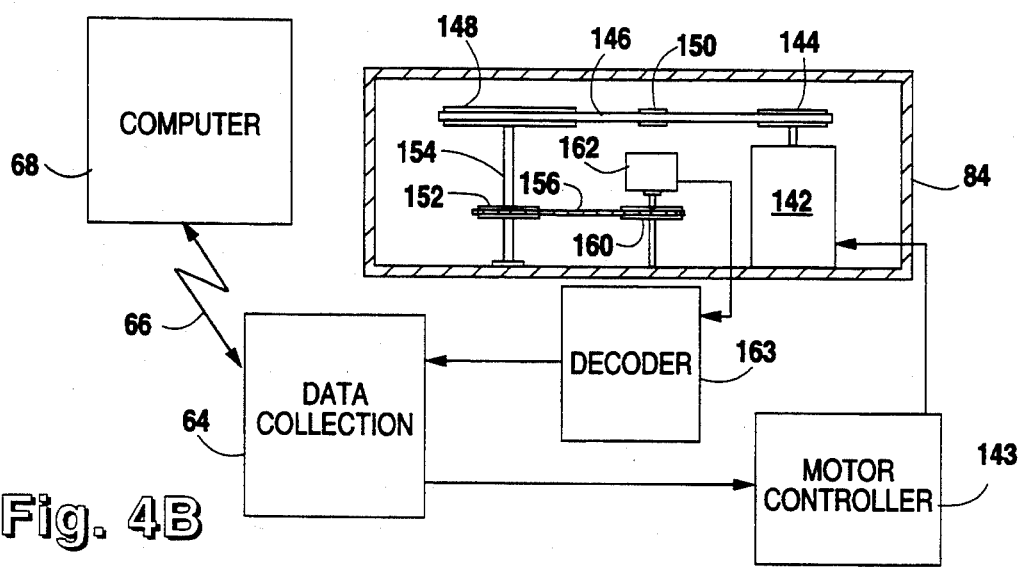
FIG. 4B is an illustrative drawing of the ring drive subsystem in a side view.
Figure 5:
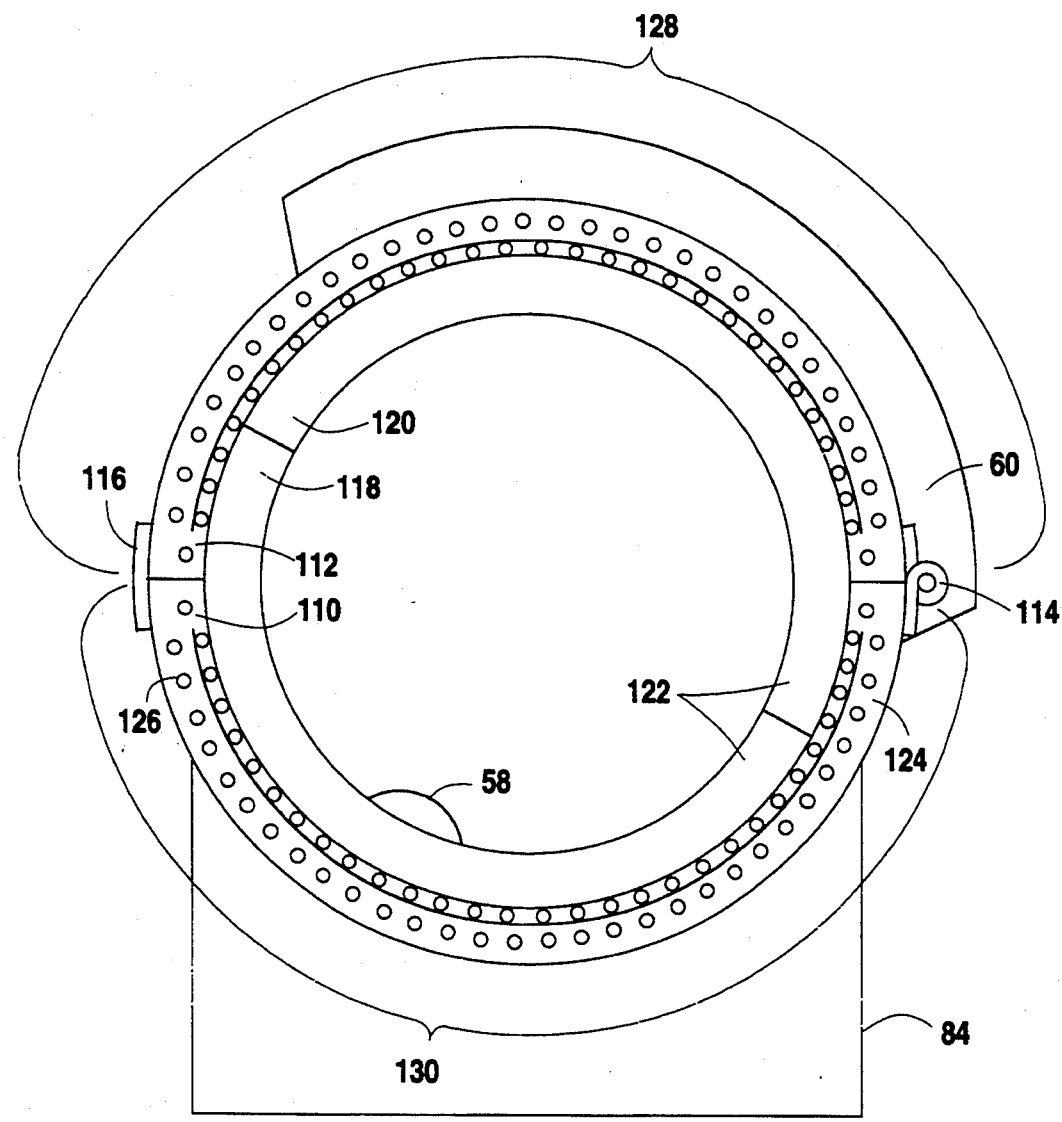
FIG. 5 is an illustrative drawing of a cross-section of the ring assembly showing the tracks of the recirculating bearings in each half of the ring assembly.

While FIG. 3 shows the gantry mechanism by which the ring assembly 54 is translated along the length of the steam pipe 18, FIGS. 4a, 4b, and 5 show the ring assembly mechanisms by which the source 58 and detector array housing 60 apparatuses are rotated about the axis of the steam pipe 54. One half of the outer ring 110 of the ring assembly 54 is mounted to the yoke 84 and is held in a fixed position while the other half of the outer ring 112 is free to open and close about a hinge 114 and be locked in a fixed closed position via a locking bracket 116. When the outer ring halves 110 & 112 are closed in a locked position, the inner ring halves 118 & 120 can be released to rotate freely. When the ring assembly 54 is to be opened the inner ring halves 118 & 120 are aligned with the outer ring halves 110 & 112 and held in place by pins (not shown). These pins prevent the movement of the inner ring halves 118 & 120 relative to the outer ring halves 110 & 112 when the ring assembly 54 is opened.

In an alternative embodiment of the present invention the two ring halves can be joined together with two mounting brackets 116; a hinge 114 is not necessary.

FIG. 5 is an illustrative drawing showing how the inner and outer rings 122 & 124 act as a large recirculating ball bearing when the ring assembly 54 is locked in a closed position and the inner rings halves 118 & 120 are released. The outer ring 124 is held in a fixed position by the yoke 84 while the inner ring 122 is free to rotate on ball bearings 126. The ball bearings 126 on which the inner ring 122 rotates roll in two recirculating tracks 128 & 130. These tracks 128 & 130 are seated in the outer ring halves 110 & 112 and remain fixed relative to the outer ring halves 110 & 112. The use of two independent recycling tracks 128 & 130 and pins (not shown) to hold the inner half rings in place enables the ring assembly 54 to be opened without loss of ball bearings 126.

Returning to FIGS. 4a and 4b, the inner ring 122 bears a toothed surface 140 about its periphery by which the rotation of the inner ring 122 is controlled. The rotation of the inner ring 122 is actuated by an electric motor 142. The motor 142 rotates a pulley 144. The pulley 144 drives a belt 146 which turns a second pulley 148 of larger diameter than the pulley 144 attached to the motor 142. The ratio of the diameters of these pulleys 144 & 148 is known. Tension is maintained in the belt 146 by a tensioning pulley 150. A sprocket 152 is mounted on the same axil 154 as the larger pulley 148 as shown in FIG. 4b. This sprocket 152 drives a chain 156 which in turn drives two additional sprockets 158 & 160 of the same diameter as the first sprocket 152. One sprocket 158 is positioned proximate to the toothed surface 140 of the inner ring 122 maintaining contact between the chain 156 and the inner ring's toothed surface 140 so that the chain 156 drives the rotation of the inner ring 122 when the sprockets 152, 158 & 160 rotate. The other sprocket 160 is attached to an optical encoder 162 which encodes the rotation of the sprocket 160. The method used to optically encode the rotation of the sprocket 160 is described in greater detail below. Since the circumference of the inner ring's toothed surface 140 and the circumference of the sprocket 160 is known, monitoring the rotational position of the sprocket 160 enables the calculation of the position of the inner ring 122. Tension in the chain 156 is also maintained by a tensioning wheel 164.

OPTICAL ENCODING

As was described above, the rotation of the threaded rod 88 and the rotation of the sprockets 152, 158 & 160 that rotate the inner ring 122 of the ring assembly 122 are both optically encoded. Nevertheless, other methods of monitoring the longitudinal position of the ring assembly 54 and the rotational position of the inner ring 122, other than optical systems are possible.

Figure 6A:
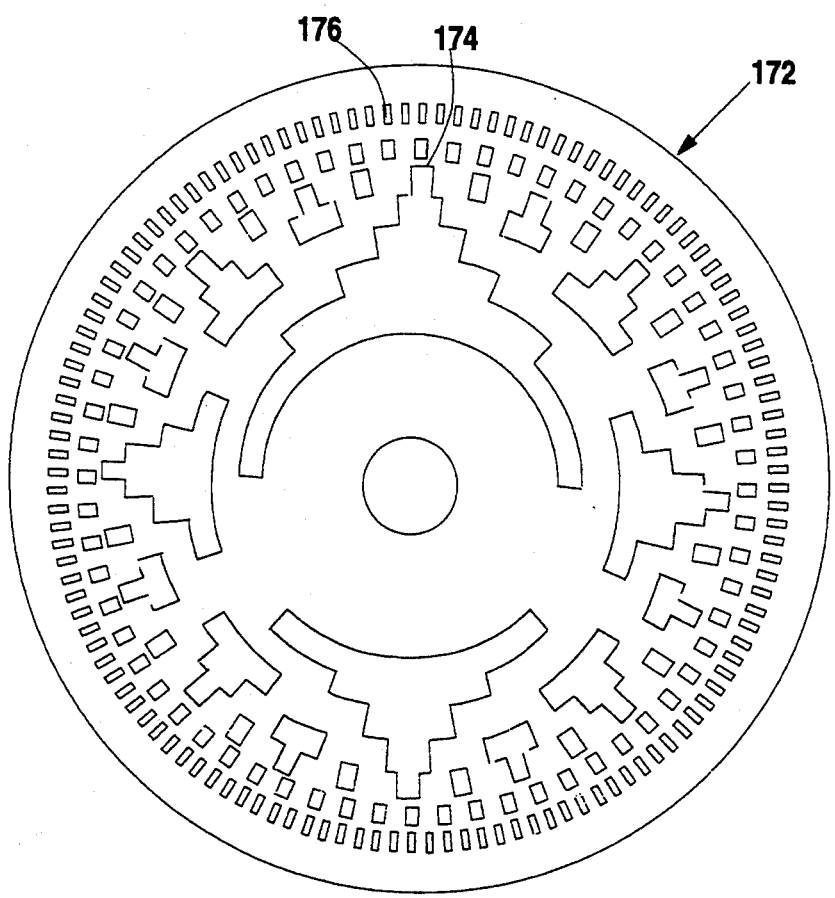
FIG. 6A is an illustrative drawing of the encoder wheel of an absolute position optical encoder.

There are two general types of optical encoders: incremental encoders and absolute position encoders. Although an incremental optical encoder is suitable, an absolute optical encoder is preferable since it can be used to determine not only rotation but also direction of rotation and precise angular position rather than simply a change in position. An absolute optical encoder disk 172 is shown in FIG. 6a. The disk 172 has multiple tracks 174 with slots 176 cut out. The disk 172 rotates between light emitting sources (not shown) and light sensors (also not shown). One pair of light emitting sources and light sensors are positioned along each track of the absolute optical encoder disk 172. As the disk 172 rotates the slot patterns on each track 174 of the disk 172 pass by the tracks 174 corresponding light source/sensor pair. When a slot 176 is positioned between the source/sensor pairing, the light sensor senses light. When no slot 176 is present, the sensor does not sense light. Thereby, each source sensor pair generates a digital signal.

Figure 6B:
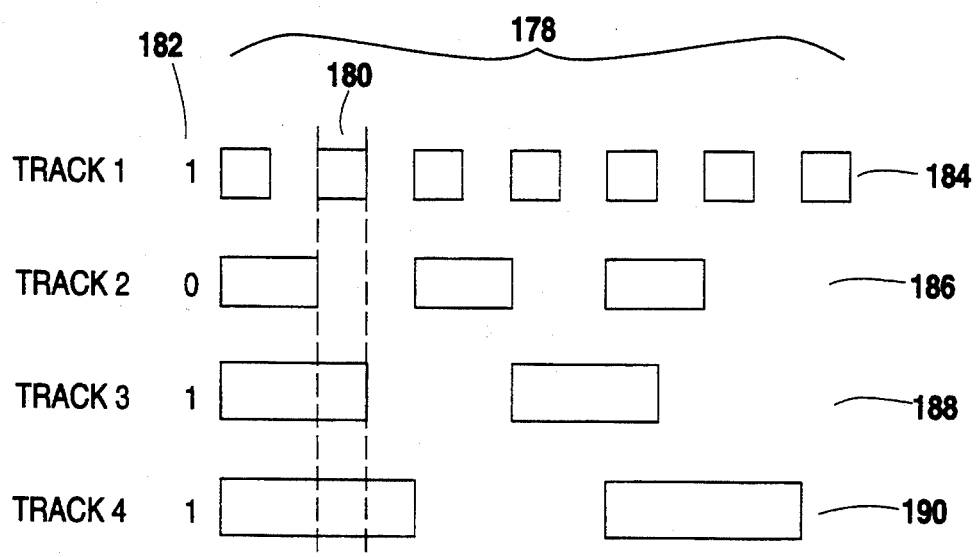
FIG. 6B is an illustrative drawing showing several rotational positions of the wheel and their respective codes encoded.

FIG. 6b shows an example of a typical slot pattern 178 as seen by four sensors [not shown]. In the disk's 172 current position 180, the code 182 generated by the sensors in the four tracks 184, 186, 188 & 190 is "1011". Each position 180 around the disk 172 has a unique code 182. The number of position 180 is determined by the number of tracks 174 on the encoder disk 172.

The coded signals generated by the sensors in the optical encoder 162 are transmitted via hardwire 107 to a decoder 108 which converts the encoded signal into meaningful positional data. The decoders 108 (FIG. 3) decode the signal and transmit it along the optical fiber transmission system 66 to the computer 68.

Since the codes 182 are unique for each position 180 of the encoder disk 172, the direction of rotation can be determined by comparing one position 180 reading with the previous position reading.

For the present invention, a conventional, multi-turn absolute optical encoder and accompanying decoder with a rotational resolution of 1024 positions per 360 degrees, and 512 turns is suitable.

THE SOURCE

Figure 7:
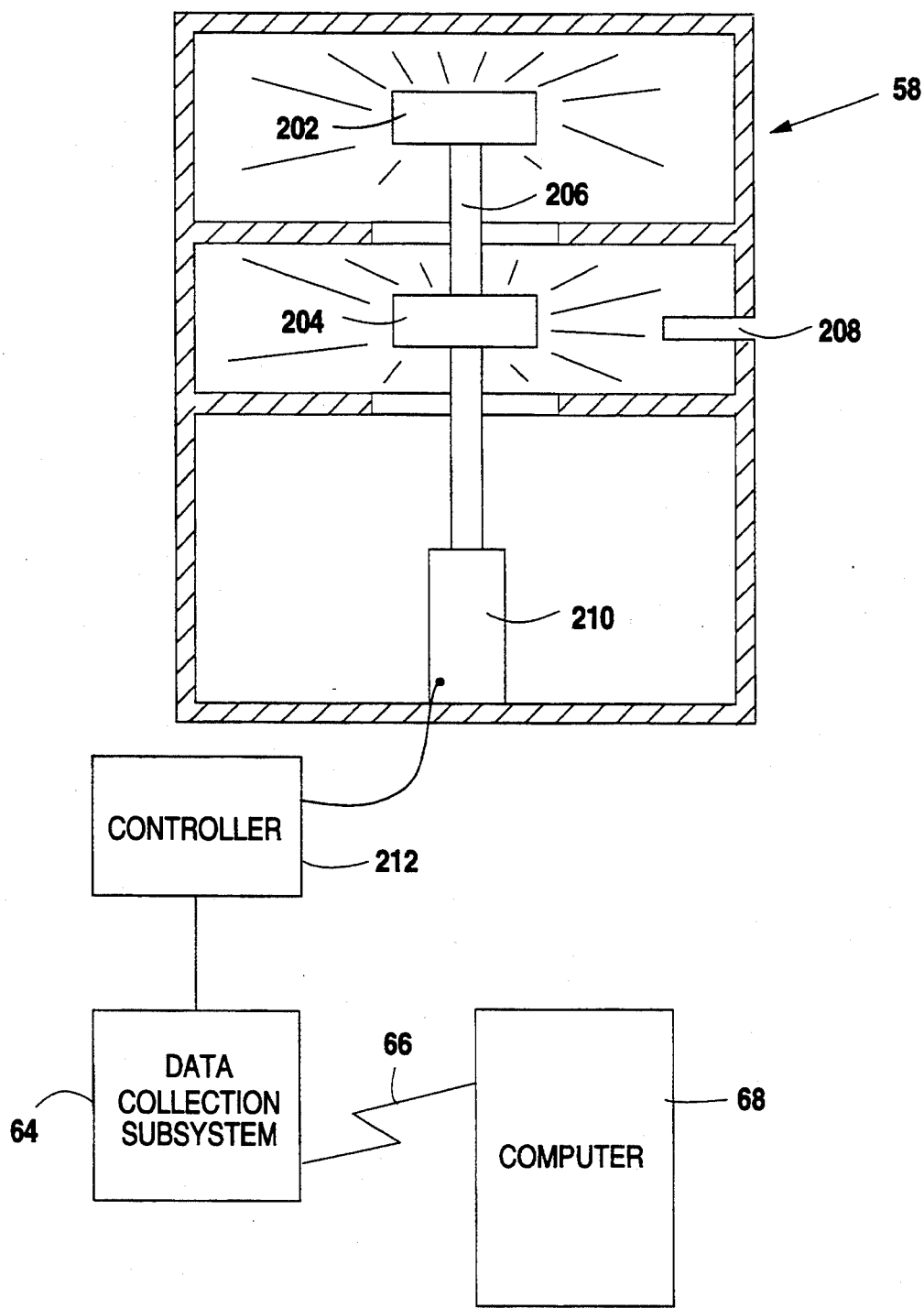
FIG. 7 is an illustrative drawing showing the source assembly and two penetrating radiation sources.

FIG. 7 is a more detailed depiction of the penetrating radiation source assembly 58. As shown in FIG. 2, the source assembly 58 is mounted on inner ring half 118 of the ring assembly 54.

The source assembly 58 preferably contains two radioactive source pellets 202 and 204. Since the material which is being scanned may not have uniform density throughout, it is useful to be able to scan the component with radiation from different sources. One example of the importance of the ability to scan components of non-uniform density is pipe welds. The density of the material around and in a pipe weld is not uniform with the rest of the pipe. Cobalt and iridium radioactive sources emit suitably different radiation for the described purposes, although other radiation sources may also be suitable.

The source pellets 202 and 204 are mounted on a tungsten rod 206. This tungsten rod 206 can be moved in order to position one of the source pellets 202 and 204 into the beam port 208. FIG. 7 shows the cobalt source pellet 204 in the beam port 208. The steel rod 206 is driven by an air solenoid 210.

The controller 212, which controls the movement of the tungsten rod 206 and source pellets 202 and 204, provides the system operator with three setting choices for operating the source 58: Off, Manual and Automatic. In the Off setting the tungsten rod 206 can not be moved. In the Manual setting either source pellet 202 or 204 can be chosen to be in the beam port 208. In the Automatic setting, the movement of the tungsten rod 206 is controlled by the system computer 68.

THE DETECTOR ARRAY

Figure 8A:
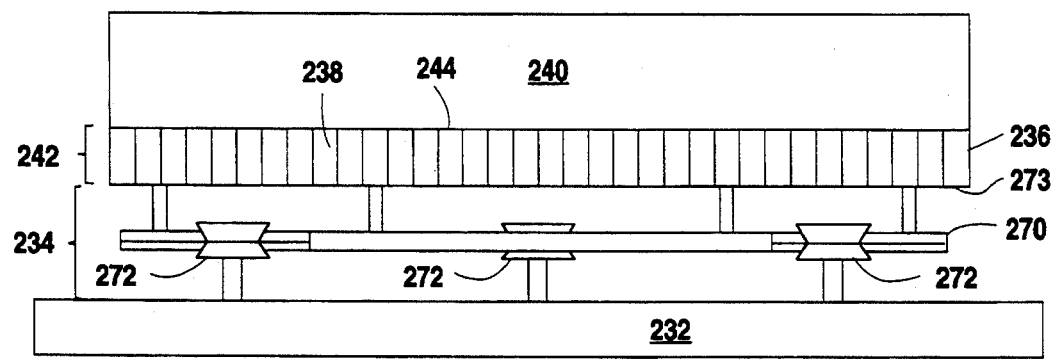
FIG. 8A is an illustrative drawing showing the components within the detector housing as seen from the source.
Figure 8B:
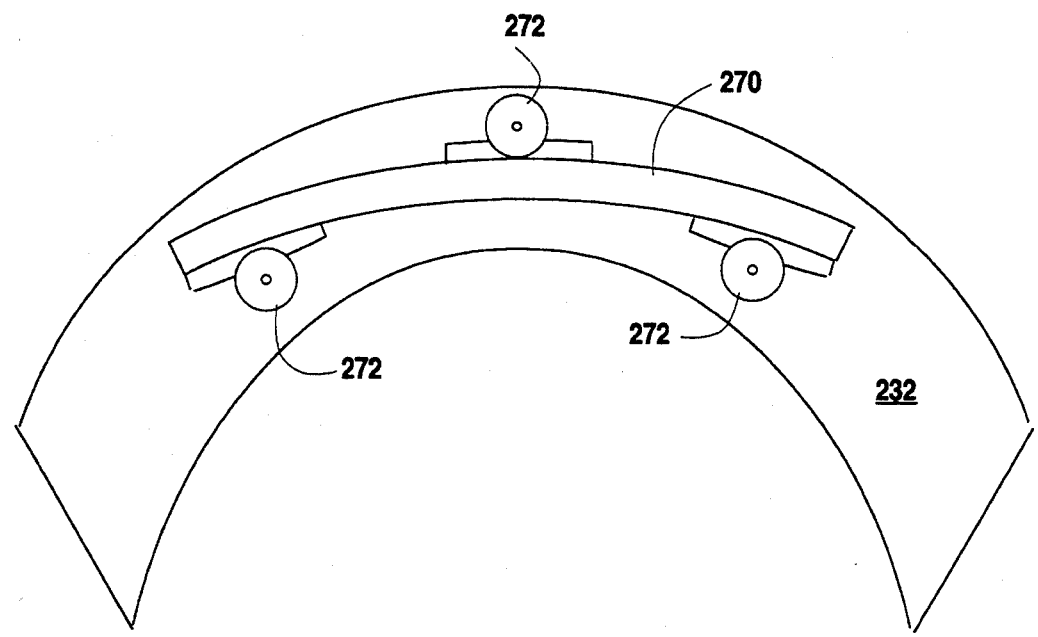
FIG. 8B is an illustrative drawing of the detector array as seen from the top of the detector housing.

FIGS. 8a and 8b show the contents of the detector array housing 60: the base plate 232, the sub-positioning components 234, the detector guide plate 236 the individual detectors 238 and the signal conditioning electronics 240.

The detector array 242 consists of a plurality of individual radiation detectors 238. The detector guide plate 236 has a plurality of slots 244 into which the individual detector units 238 are fitted. These detectors 238 are slid into these slots 244 in the detector guide plate 236 and are held in place by a ball/detent locking mechanisms (not shown).

Figure 9A:
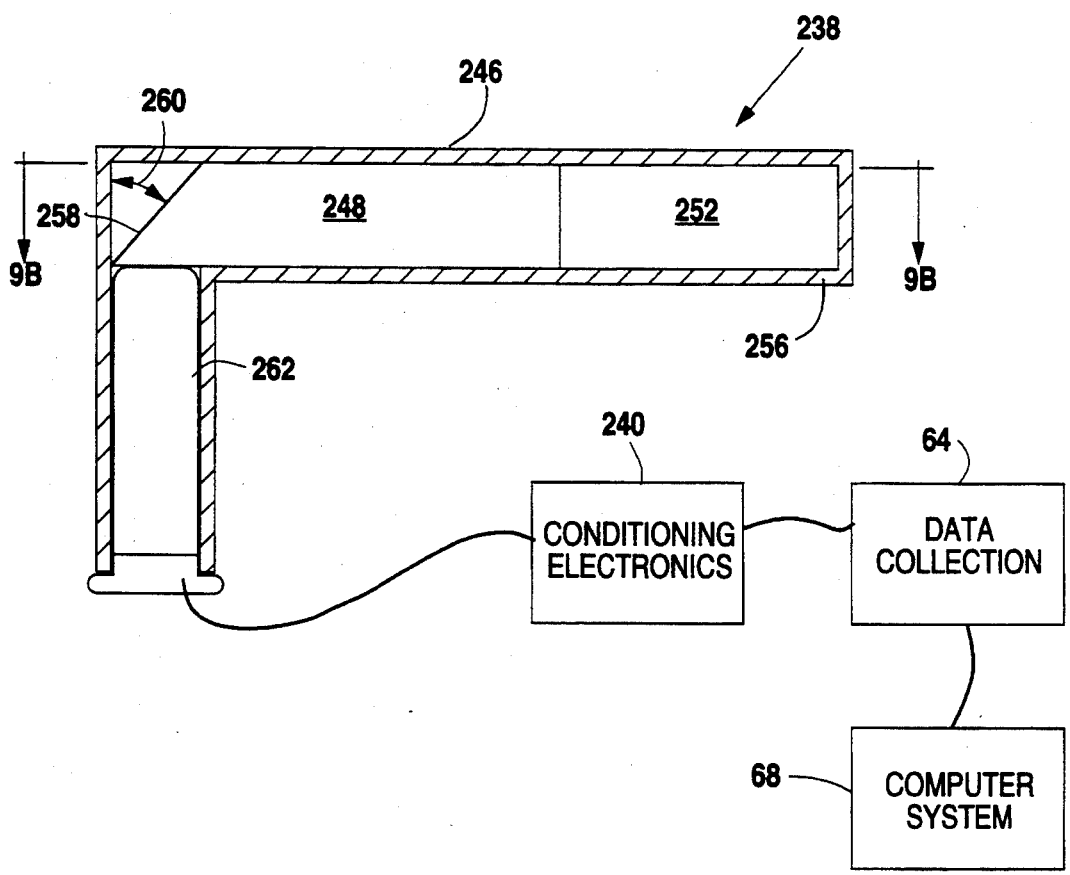
FIG. 9A is an illustrative drawing of an open individual detector showing the tungsten shielding strips, scintillating plastic and photomultiplier tube.
Figure 9B:
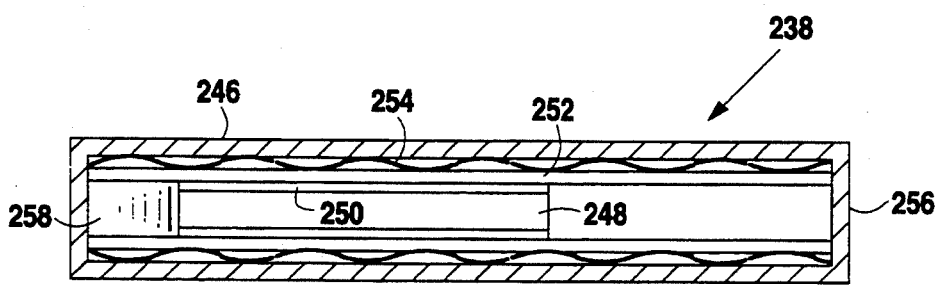
FIG. 9B is an illustrative drawing of a cross-section of a detector showing the housing and its various layers.

Each of the individual detectors 238 shown in FIGS. 9a & 9b is composed of an aluminum housing 246 which holds a section of scintillating plastic 248 wrapped in aluminum foil 250, sandwiched between two tungsten strips 252. This assembly is positioned by two wave springs 254 which apply positive pressure between the aluminum casing 246 and its contents. The tungsten strips 252 are longer than the scintillating plastic 248 and act as radiation precollimators, which limit the radiation which enters the frontal end 256 of the scintillating plastic 248 to those entering the detector 238 perpendicular to the frontal end 256 of the detector 238 in a straight line from the source 58. The tungsten strips 252 also decrease the amount of interdetector scattering radiation which is absorbed by the scintillating plastic 248. The aluminum foil 250 which is wrapped around the scintillating plastic 248 serves as a reflector which prevents light from escaping the plastic strip 248.

The scintillating plastic 248 converts the radiation signal into a light signal. The distal end 258 of the scintillating plastic 248 has a forty-five degree angle 260 which reflects light down to a photomultiplier tube 262 which is also encased in the aluminum casing 246 perpendicular to the tungsten strip 252 and scintillating plastic 248 portion of the detector 238. The photomultiplier tube 262 transduces the light signal into an electric signal, which is transmitted to the detector conditioning electronics boards 240 described in greater detail below via hardwire. The signal conditioning electronics boards 240 are mounted on top of the detector guide plate 236.

Except for minor differences included in the description before, suitable detector electronics for carrying out the present invention are described in PCT Publication No. PCT/US91/03828 entitled "An Automated system for Controlling the Quality of Geometrically Regular Shaped Products during Their Manufacture," corresponding to U.S. patent application Ser. No. 07/531,454; and U.S. Pat. No. 4,725,963, to Taylor et al., entitled "Method and Apparatus for Dimensional Analysis and Flaw Detection of Continuously Produced Tubular Objects," which are incorporated herein by reference.

Figure 9C:
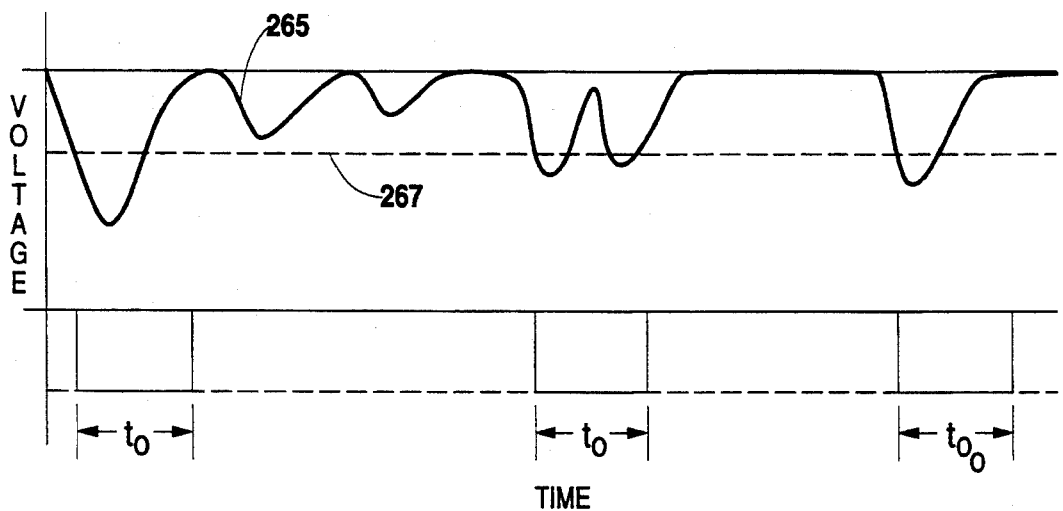
FIG. 9C is an illustration of the analog signal produced by each detector.
Figure 9D:
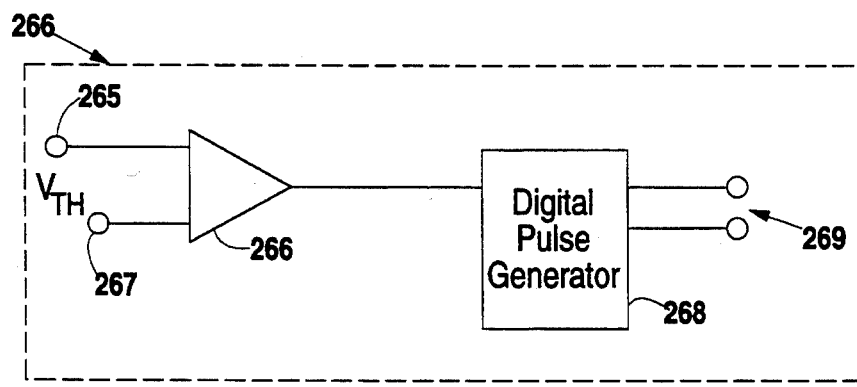
FIG. 9D is a schematic illustration of the detector analog signal conditioning electronics which prepares the signal for use by a digital system.

The detector signal conditioning electronics 240 for each detector 238 are shown in FIG. 9D. Each detector 238 generates a fast analog voltage signal 265, illustrated in FIG. 9C, in response to the gamma rays or X-rays detected by the detector 238. The analog signal 265 is transmitted to the signal conditioning subsystem 240 shown in FIG. 9D. The signal conditioning electronics 240 includes a conventional ultra-fast comparator 266 which has one input connected to the link 265 from a detector 238. The second input is connected to an adjustable voltage source $V_{TH}$ which provides the threshold voltage 267 to the comparator 266. The comparator 266 generates a trigger pulse which is then transmitted to a digital pulse generator 268. The generator 268 generates a digital pulse or conditioned signal 269 in response to a trigger pulse at its input, but only if the trigger pulse occurs after the fixed dead-time period $t_o$, as shown in FIG. 9C, prior to collection by the data acquisition control system 64. Except as described herein, suitable sources 58 and detector arrays 60 are described in U.S. Pat. No. 4,725,963, to Taylor et al., entitled "Method and Apparatus for Dimensional Analysis and Flaw Detection of Continuously Produced Tubular Objects".

Since the analog signals 265 have varying amplitudes and occur randomly due to the randomly emitted photon events from source pellets 202 & 204, the detector electronics 240 are designed to generate a digital pulse or conditioned signal 269, only when the analog signal from a detector 238 has an amplitude greater than a threshold level 267. Once triggered, the conditioning electronics 240 cannot generate another conditioned signal 269 for a fixed time period $t_o$ called "dead time." The fixed dead-time period allows for an accurate correction of the number of pulses counted.

Each detector 238 has slightly different recovery times in which it can recover from sensing one pulse and sensing a following pulse. This is due to the random nature of the incoming signal 265 pulse height and width. During a detector's recovery time, additional pulses may enter the detector 238. This piling up of pulses must be corrected for. Since each detector 238 has a different recovery time, the corrections can be complicated. To simplify the correction, the signal conditioning electronics 240 sets a fixed dead time, uniform for each detector, which is greater than the largest recovery time. By using a fixed dead time, the proportion of time for which the detectors do not respond to incoming radiation is known. Knowing this proportion, the measured radiation count can be corrected to account for the total actual radiation which entered the detector. For example, if the measured radiation count was 900 and the total dead time accounted for 10% of the total time, the actual radiation count is calculated to be 1000. Using a uniform fixed dead time for all detectors allows the use of one formula for all the detectors 238; therefore, it is not necessary to determine the response time of each individual detector.

The stability of the system can be improved over the electronics disclosed in PCT Publication No. PCT/US91/03828 by using a programmable high voltage source (not shown) instead of a set high voltage source (also not shown) to the photomultiplier tube 262. Since the high voltage affects the gain of the system, a programmable voltage source allows for programmable gain thereby allowing the sensitivity of all detectors to be adjusted similarly, thus increasing the stability and accuracy of the system.

The detector guide plate 236 is mounted on top of the detector housing base plate 232 through a sub-positioning guide rail 270 and three v-grooved rollers 272. The sub-positioning guide rail 270 is mounted to the bottom surface 273 of the detector guide plate 236, while the three v-grooved rollers 272 are mounted to the detector housing base plate 232. The detector array housing cover (not shown) is mounted on top of the detector array base plate 232 in such manner as to cover the contents of the detector array 242, sub-positioning mechanism 234, and detector conditioning electronics 240. The back wall (not shown) of the detector array housing 60 is lined with a lead or tungsten shield (not shown) to block stray radiation that is not attenuated by the detectors 238.

SUB-POSITIONING OF THE DETECTOR APPARATUS

In addition to scanning the components 18 by translating along its length, and rotating around the components via the gantry 52, yoke 84 and ring assembly 54 described above, the present invention also shifts the detector array subassembly 242 relative to the source 58 and detector base plate 232 in order to increase the density of scanning data collected and to cover blind spots caused between the scintillating plastic of the detectors 238. This technique is called sub-positioning. The sub-positioning guide rail 270 and v-grooved rollers 272 mentioned above are key to sub-positioning of the detector array 242. The v-grooved rollers 272 which are fixed to the detector housing base plate 232 allow the sub-positioning guide rail 270 to move relative to the base plate 232. Since the detector guide plate 236 is fixed to the sub-positioning guide rail 270 the detector guide plate 236 moves along with the sub-positioning guide rail 270 and the whole detector array 242 moves relative to the detector base plate 232. Since the detector base plate 232 is in a fixed position relative to the source 58, the detector array 242 also moves relative to the source 58 when the sub-positioning guide rail 270 moves.

Figure 10A:
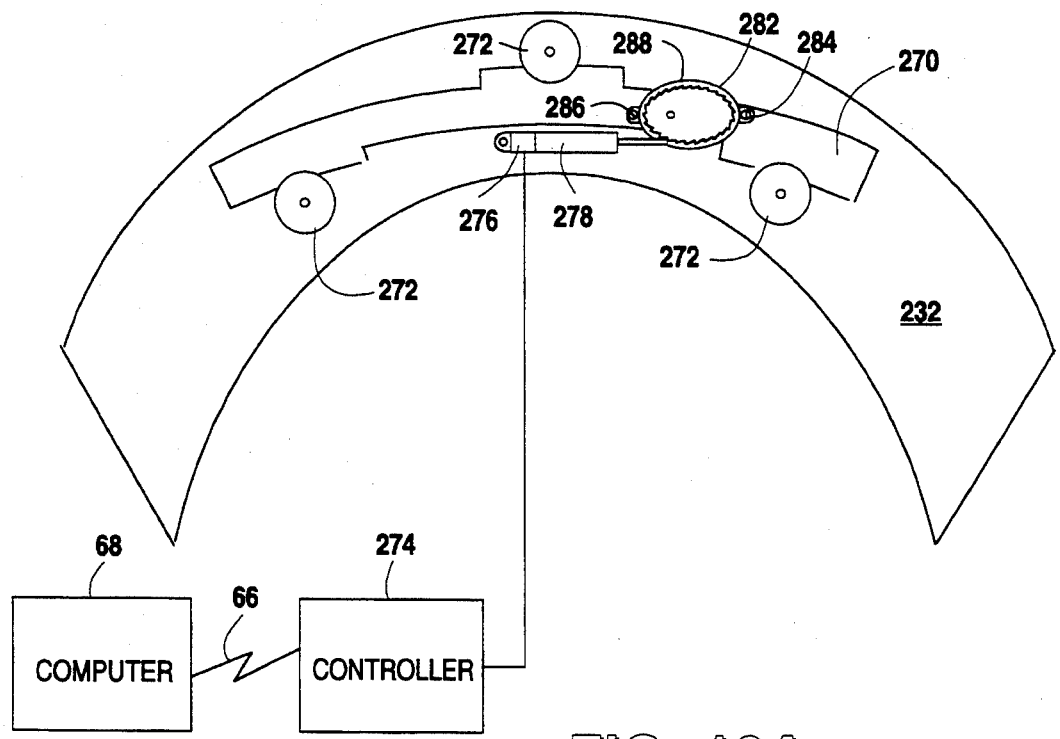
FIG. 10A is an illustrative drawing of an air driven ratchet and pawl sub-positioning actuator system.

FIG. 10a shows one actuation system for moving the sub-positioning guide rail 270. A controller 274 receives control data from the computer system 68 and sends a signal to a valve 276 which allows pressurized air to flow into or out of a pneumatic cylinder 278 which is mounted to the detector housing base plate 232. The extension of the rod 280 in the pneumatic cylinder 278 rotates an eccentric cam 282 which is also mounted to the detector housing base plate 232. As the eccentric cam 282 rotates, two rollers 284 & 286 attached to the sub-positioning guide rail 270 move to remain tangential to the outer surface 288 of the cam 282. Since the cam 282 is eccentric it forces the sub-positioning guide rail 270 to move relative to the detector housing base plate 232 to which the cam 282 is attached.

Figure 10B:
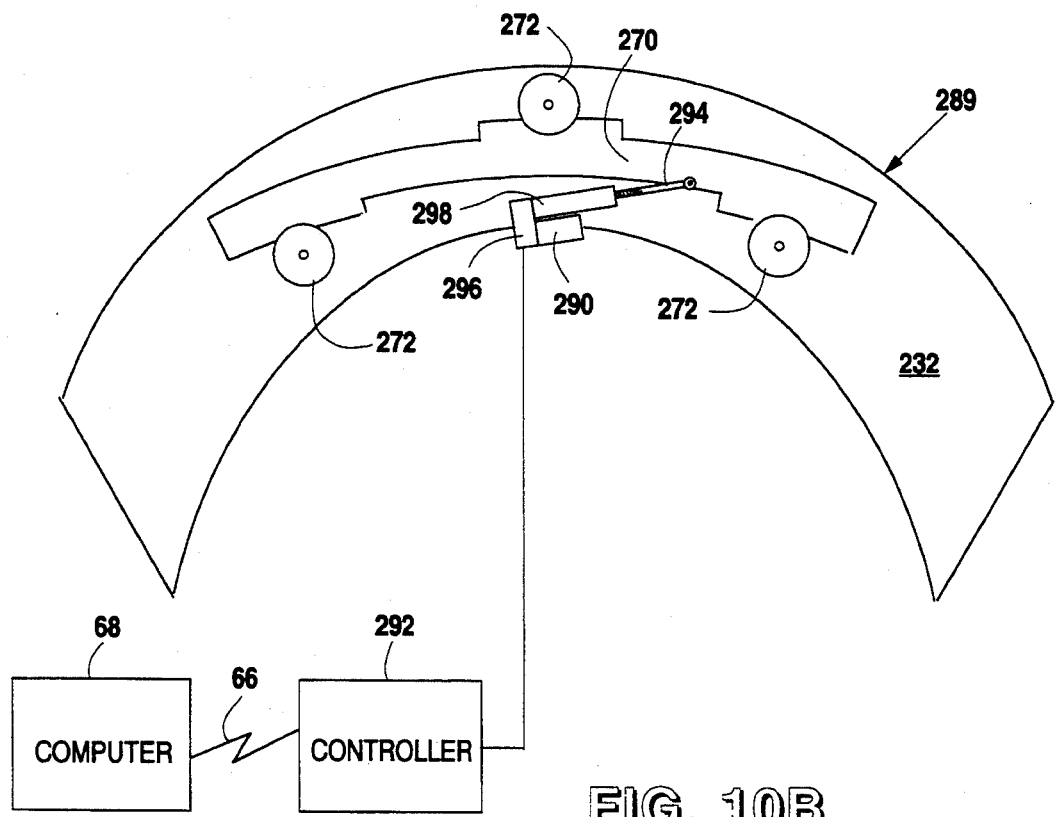
FIG. 10B is an illustrative drawing of a electric motor driven sub-positioning actuator system.

FIG. 10b shows an alternative actuation system 289 for moving the sub-positioning guide rail 270. In this embodiment the sub-positioning guide rail 270 is caused to move by a motor 290 which receives signals from a controller 292. The motor 290 cause a screw rod 294 to turn through a transmission system 296 and thereby extend out of its housing 298. The end of the screw rod 294 is attached to the sub-positioning guide rail 270 is such a manner so as to allow movement when the threaded rod 294 extends from its casing 298. The motor and screw rod sub-positioning actuation system 289 must be mounted to the detector housing base plate 232 in such manner as to allow the assembly 289 to freely rotate enough to account for the nonlinear path the portion of the rod screw 294 attached to the sub-positioning rail 270 must travel.

SYSTEM GEOMETRY

Figure 11:
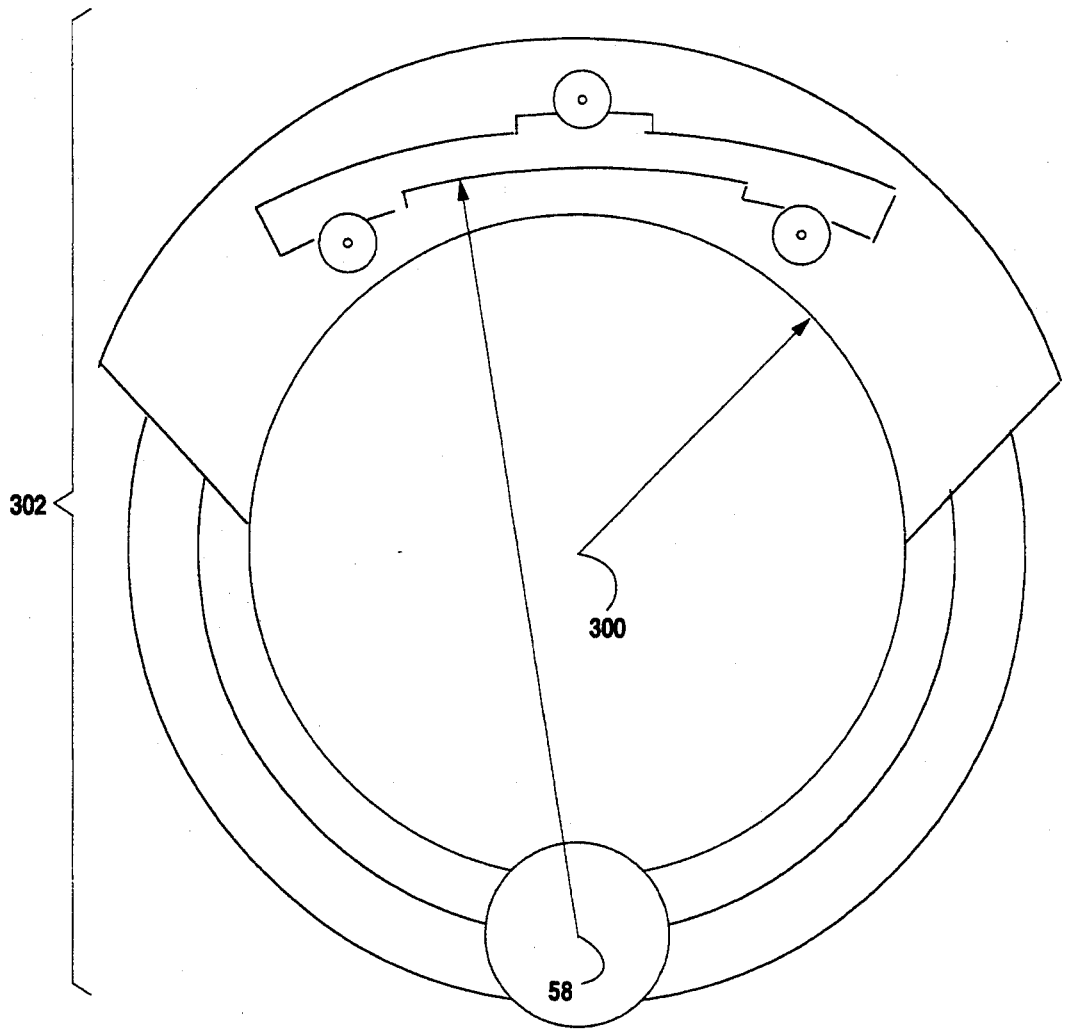
FIG. 11 is an illustrative drawing of the geometry of the detector array about the ring center and the sub-positioning guide-rail about the source.

FIG. 11 illustrates the geometry of the source 58 /detector array 242 /sub-positioning 234 systems. The detector array 242 positions the detectors 238 in an arc of a circle centered at the center of the ring assembly 300. Although this structure complicates the calculations required to use the data collected from scanning an component 18, an object-centered detector array system can be constructed with an overall smaller system diameter 302 than a source-centered detector array system. In applications where the scanning apparatus must maneuver between support structures around the component scanned, the size of the system can be of significant importance. However, while the detector array 242 is centered around the center of the ring assembly 300, each individual detector 238 is oriented at different angles as though the source 58 is the center of the system. Likewise the sub-positioning guide rail 270 is structured to move along an arc of a circle centered at the source 58.

THE SAFETY AND ENVIRONMENTAL CONTROL SYSTEM

The disclosed apparatus is also equipped with safety and environmental control equipment and safeguards. The trailer, shown in FIG. 2, which holds the computer 68 and all its periphery 70, has a separate thermostat and heating and air conditioning system (not shown). This keeps the temperature inside the trailer 50 fairly consistent and comfortable for the system operators. The rest of the safety and environmental control system is controlled by the computer 68 which receives signals from temperature and radiation sensors (not shown) and sends control signals to various components of the system.

The data collection subsystem 64 contains an air conditioner (not shown) and temperature and radiation sensors (also not shown). The air conditioner keeps the inside of the data collection subsystem housing 64 cool and maintains positive air pressure inside the housing 64 to help prevent dust and debris from entering the housing 64. The temperature sensor provides feed back to the air conditioning system. Both the temperature and radiation sensors transmit data to the computer system 68 in the trailer 50. If the temperature or radiation levels rise to a predetermined level and the computer system 68 transmits a warning message to an annunciator peripheral 70 inside the trailer 50 and out in the facility where the scanner is being used.

The data collection subsystem 64 also contains a second air conditioning system (not shown). This air conditioning system sends cold air to the detector array housing 60 via the umbilical cord 62. Positive air pressure is also maintained in the detector array housing 60 to help keep out dirt and other debris. Temperature and radiation sensors (not shown) are also placed in and around the detector array housing 60. These sensors transmit information to the computer system 68 which will also activate annunciators peripheral 70 if temperature and-/or radiation levels rise to predetermined levels.

DATA ACQUISITION

Figure 12:
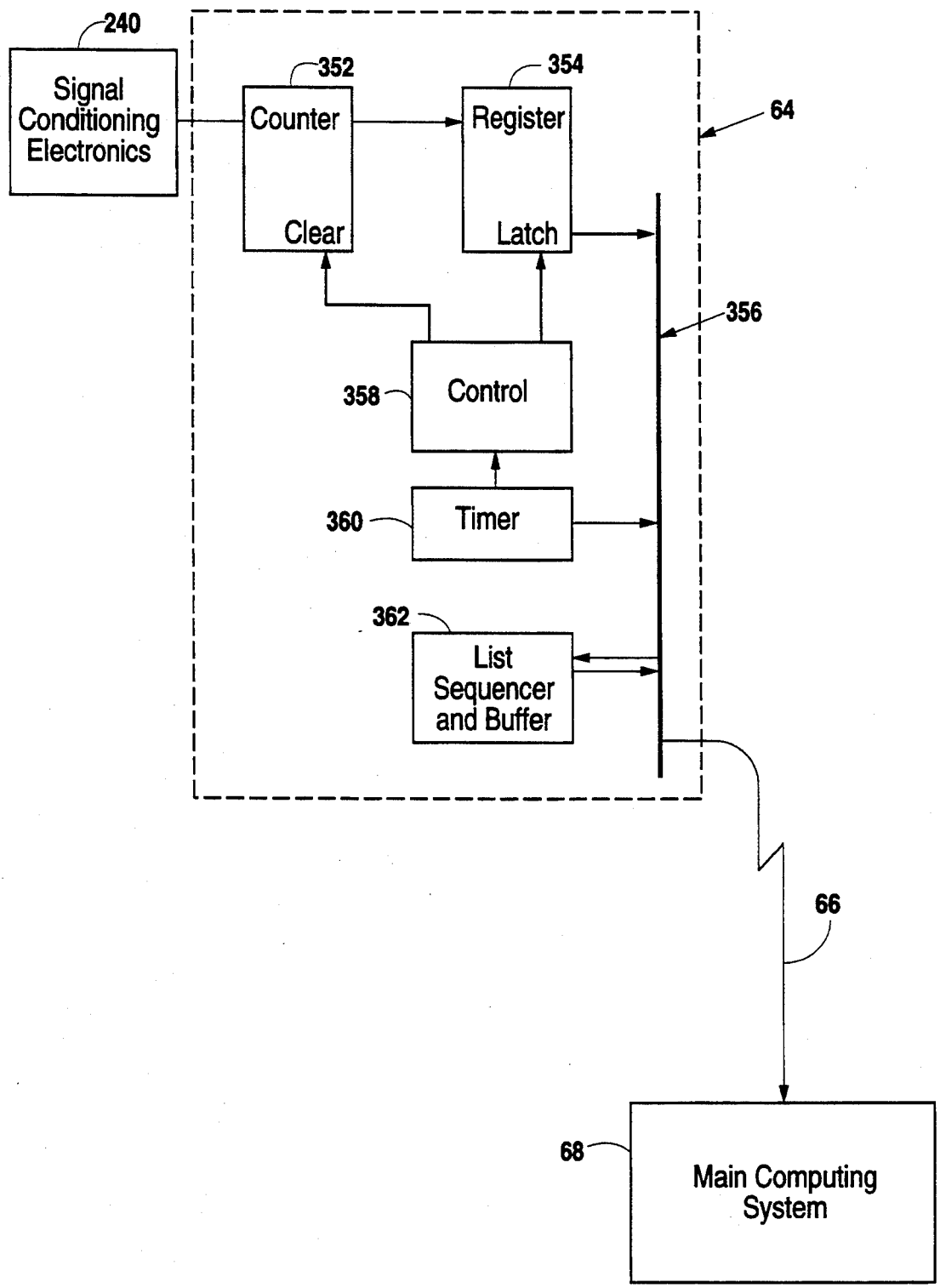
FIG. 12 is a schematic diagram of the data collection control subsystem.

A suitable data collection system 64 for use with the Apparatus herein is shown in FIG. 12, which is also more particularly described in PCT Publication No. PCT/US91/03828 entitled "An Automated system for Controlling the Quality of Geometrically Regular Shaped Products during Their Manufacture". FIG. 12 depicts how data from each detector 238 is collected and transmitted from the signal conditioning subassembly 240 to the computer system 68. The digital signals coming from each detector's signal conditioning electronics 240 is transmitted to a conventional counter 352, which continuously counts the number of times the signals exceed a predetermined threshold value. A data register 354 periodically latches onto the count in the counter 352 at a predetermined sampling rate and transmits the count to the data acquisition subsystem data bus 356. Immediately after the register 354 latches onto the count, the counter 352 is cleared and continues counting from zero. The latching of the register 354 and clearing of the counter 352 is effectuated by a conventional controller 358. The controller 358 has, at its disposal, a timer 360 which transmits time information to the controller 358 and the data bus 356. A suitable list sequencer and buffer 362 collects data sent from the data register 354 and blocks the data in compact format before sending the data to the computer system 68, via a suitable high-speed communication link 66 capable of transmitting 32 bit words at a rate up to 5 megabytes per second. A suitable high-speed communications link 66 is a fiber optic connection with 100 micrometer optical fiber core with attenuation of 5 dB/Km or less.

SCANNING MODES

The present invention can be operated in two categories of scanning modes: gauging modes and analytical modes. The distinguishing characteristics between these two categories of scanning modes is the number of actual scans made and the methods used to analyze the data collected.

GAUGING MODE

In the gauging mode, the computer 68 is programmed to employ limited angle data collection and analysis methods described in U.S. Pat. No. 4,725,963, to Taylor et al., entitled "Method and Apparatus for Dimensional Analysis and Flaw Detection of Continuously Produced Tubular Objects" and PCT Publication No. PCT/US91/03828 entitled "An Automated system for Controlling the Quality of Geometrically Regular Shaped Products during Their Manufacture," except that the programming must be adapted to an object-centered detector array system geometry as described above rather than a source-centered detector array system geometry.

The programming must be adapted to this new geometry because the intensity of the gamma ray signal entering each individual detector is a function of the distance from the source to the detector. In a source-centered detector array system geometry, this distance is equal for all detectors; while, in a object-centered detector array system geometry this distance varies. The intensity of the gamma ray signal as detected by the detector is a function of the following ratio:

$$1/r^2$$

where "r" is the distance from the source to the detector.

One of the first calculations required in the gauging mode is to determine the length of material in the paths between the source 58 and each detector 238. This is possible because the presence of a solid object, such as pipe in the path of the gamma rays, attenuates the gamma ray signal received by the detector 238. The greater the length of material the gamma rays must travel through, the greater the attenuation of gamma rays.

However, to calculate the path lengths for a set of scaler data, the computer system 68 must have access to two additional sets of scaler data: the background count rate and the air count rate. The background count rate is obtained while the radiation source 58 is closed; the air count rate is obtained while the radiation source 58 is open, with no solid objects in the path of the gamma ray beam.

Before using the air count rate and the pipe attenuated count rate in any calculations, these count rates must be corrected for the interval of time that the signal conditioning electronics 240 is inhibited by the detection of a gamma ray pulse. During this time, gamma rays are entering the detectors 238, but are not being counted. This short interval of time, described earlier as "dead time," is accounted for by the following formulas:

$$A_i' = A_i / [1 - A_i(T_1/T_2)]$$

$$P_i' = P_i / [1 - P_i(T_1/T_2)]$$

where "i" ranges from 1 to the maximum number of detectors 238, "$A_i$" represents the air count, "$P_i$" represents the pipe attenuated count, "$T_1$" represents the time that the analog signal 265 is inhibited after a pulse is detected; "$T_2$" represents the data acquisition time, and "$A_i'$" and "$P_i'$" represent the dead-time corrected count rates.

"$T_1/T_2$" is typically approximately $1.5 \times 10^{-6}$, and the quantities $A_i(T_1/T_2)$ and $P_i(T_1/T_2)$ are much less than 1 in practical applications. It is normally not necessary to correct the dead time for the background count rate because the count rate is slow enough that the correction is insignificant.

After dead-time corrections have been made to the air count and pipe attenuated count, the background count, "$B_i$", is subtracted from the pipe attenuated count and the air count:

$$A_i'' = A_i' - B_i$$

$$P_i'' = P_i' - B_i$$

where "$A_i'$" represents the air count after being corrected for dead time, and "$P_i'$" represents the pipe attenuated count after being corrected for dead time.

After the dead time and background count corrections have been completed, it is also necessary to correct for radiation that has deviated from its path and undesirably entered into a detector out of line of its original path. This radiation is called "scattered radiation." Scattered radiation is a by-product of the interaction of the gamma rays with the atoms in the pipe. The attenuation is caused by gamma rays hitting atoms in the wall of pipe and being absorbed or scattered. Unfortunately, some of the scattered radiation is picked up by detectors 238, not originally in the line of the radiation as it leaves the source. The detector 238 readings are therefore corrected to account for the proportion of the count caused by scattered radiation rather than direct transmission. However, before completing this task, the air count and pipe count data are normalized as if each had a constant flux of radiation. This step is necessary because each detector 238 has uncontrollable differences in radiation detection efficiencies which must be normalized when considering the count rate corrections in a detector based on the count rate in neighboring detectors. The normalized air count rates, $A_i'''$, and pipe count rates, $P_i'''$, are:

$$A_i''' = C/D_i^2$$

$$P_i''' = P_i''[A_i'''/A_i'']$$

where "C" is a constant, "$D_i$" is the source to detector distance, "$A_i''$" and "$P_i''$" are the dead time corrected, background subtracted air and pipe count rates, respectively. The "$D_i^2$" term corrects the constant radiation flux rate for differences in distance between the sources and each detector.

After the pipe attenuated count rate has been normalized, corrections can be made for radiation scattering caused by the detectors 238 themselves, rather than the pipe. This type of scattering is commonly called "interdetector secondary scattering." Corrections for interdetector secondary scattering are accounted for by:

$$P_i'''' = P_i''' - \Sigma_j [N_j(P_{i+j}''' + P_{i+j}''')]$$

where "J" and the "$N_j$" are determined empirically from calibration measurements.

A final correction to the count rate is attributed to radiation scattering from the pipe itself and other supporting construction materials. This correction is proportional to the count rate and does not consider variations from detector to detector. The fully corrected count rates are then:

$$P_i''''' = P_i'''' - BA_i'''$$

where "B" is determined empirically from calibration measurements.

Path lengths are calculated using "$P_i''''$" and "$A_i''''$" through the formula:

$$L_i = F \ln(A_i'''' / P_i'''')$$

where the value of "F" is related to the X-ray absorptivity, "$\mu$" and density, "P", by $$F = (1/\mu P)$$

The X-ray absorptivity is dependent upon the X-ray energy and pipe chemical composition. The pipe material density, p, depends upon the chemical composition and temperature.

Finally, the path lengths are corrected to account for the nonlinearity of path lengths from one detector 238 to the next. This is done with the following quadratic formula:

$$L_i' = X_i + (Y_i)(L_i) + (Z_i)(L_i)^2$$

where "$L_i'$" is the corrected length, "$L_i$" is the uncorrected length and "$X_i$", "$Y_i$" and "$Z_i$" are factors which were determined by the calibration measurements discussed below.

After calculating path lengths, the computer system 68 performs a data reduction task to determine which data points will be used to calculate the outside diameter and inside diameter of the pipe and then corrects the data points for an aperture size as described below.

The data is reduced through the use of the following analysis. The detector array 60 sees a shadow of the pipe of varying intensity. This shadow is commonly called the pipe profile. There is a sharp difference where the shadow begins on the detector array 60. Continuing along the length of the detector array 60, the shadow becomes progressively darker. The shadow becomes distinctly lighter again where the inner diameter of the pipe begins. From the point where the inside diameter begins until the center of the pipe, the shadow becomes progressively lighter. After the center of the pipe, the shadow becomes darker until it become distinctly darker where the inner diameter ends. At the point the inner diameter ends, the shadow becomes progressively lighter until the shadow abruptly ends. These distinct changes in the shadow are used to determine the inside and outside diameters of the pipe.

However, prior to performing these calculations, the data points must be corrected for aperture size by indexing a table containing values appropriate for the specified size of pipe that is being inspected. In this way, the number of and distance between the path length data points which will be used in further calculations is determined.

Since the edges of the inside diameter may not correspond to the index set by the outside diameter indexing determination above, the index to be used to calculate the inside diameter is offset from the starting outside diameter index by the following formula:

$$Index = INTEGER\ (C_1 + (wall)(C_2))$$

where "$C_1$" and "$C_2$" are constants.

Figure 13:
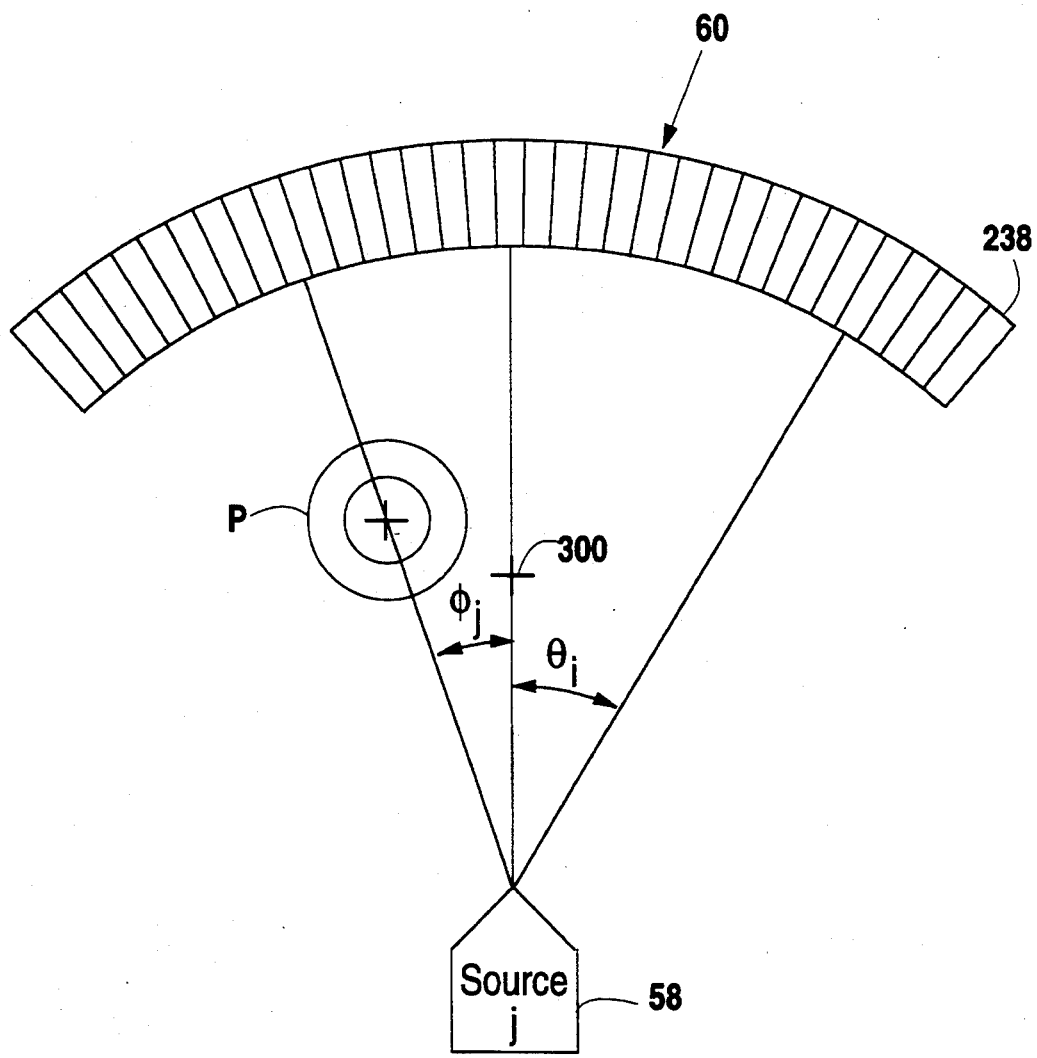
FIG. 13 is a simplified diagrammatic representation showing parameters used in the calculation algorithms.

The first calculation executed is to determine the angle to the pipe center, as seen by the detector array 60. The calculation executed $$\phi_j = \tfrac{1}{2} ARCTAN \frac{2A_1A_5 - A_2A_4}{2A_3A_4 - A_2A_5}$$

where "$\Phi_j$" represents the angle from source j 58 between the pipe center and the system center 300 (see FIG. 13), "j" ranges from 1 to n (one for each rotational scan position), "$L_i$" represents the path length as measured by the ith detector 238, and $$A1 = \tfrac{1}{2}[\Sigma_i \cos^2\theta_i - 1/N(\Sigma_i \cos 2\theta_i)^2]$$

$$A2 = \Sigma_i \sin 2\theta_i \cos 2\theta_i - 1/N(\Sigma_i \sin 2\theta_i)(\Sigma_i \cos 2\theta_i)$$

$$A3 = \tfrac{1}{2}[\Sigma_i \sin^2\theta_i - 1/N(\Sigma_i \sin 2\theta_i)^2]$$

$$A4 = \Sigma_i (L_i/2)^2 \cos 2\theta_i - 1/N[\Sigma_i (L_i/2)^2 \cos 2\theta_i]$$

$$A5 = \Sigma_i (L_i/2)^2 \sin 2\theta_i - 1/N[\Sigma_i (L_i/2)^2 \sin 2\theta_i]$$

where the summation extends over the four paths lengths, two on each side of the pipe and "$\theta_i$" represents the angle from source j 58 between the center of the $i^{th}$ detector 238 and the system center 300. (See FIG. 13.)

Knowing the angle to the center of the pipe, as seen from the detector array 60, it is possible to calculate the (x,y) center by triangulation between any pair of angles using the following formulas:

$$x_j = S_j \cos\Omega_j - D \cos(\Phi_j + \Omega_j)$$

$$y_j = S_j \sin\Omega_j - D \sin(\Phi_j + \Omega_j)$$

where ($x_j$, $y_j$) is the pipe center location as determined for $j^{th}$ detector 238, "$S_j$" represents the distance from the apparatus center to $j^{th}$ source 58, "$\Omega_j$" is the angle from the system center between the $j^{th}$ source 58 and an arbitrary reference line, and:

$$D = \frac{DL + DP}{DD}$$

where $$DL = -\cos(\Phi_{j+1} + \Omega_{j+1})(S_{j+1} \sin\Omega_{j+1} - S_j \sin\Omega_j)$$

$$DP = -\sin(\Phi_{j+1} + \Omega_{j+1})(S_{j+1} \cos\Omega_{j+1} - S_j \cos\Omega_j)$$

$$DD = -\sin(\phi_j + \Omega_j)\cos(\phi_{j+1} + \Omega_{j+1})$$
$$-\cos(\phi_j + \Omega_j)\sin(\phi_{j+1} + \Omega_{j+1})$$

After the above calculations have been completed, the outside diameter as seen by each detector array 78, "j" can be calculated as follows:

$$O.D._j = 2DC_j[(TUL_j - TUR_j)/DEN_j]^{\tfrac{1}{2}}$$

where $$DC_j = [(S_j \cos\Omega_j - x_j)2 + (S_j \sin\Omega_j - y_j)^2]^{\tfrac{1}{2}}$$

$$TUL_j = \Sigma_i(L_i/2)^2\{3N - 4[(\cos 2\phi_j \Sigma_i \cos 2\theta_i) + (\sin 2\phi_j \Sigma_i \sin 2\theta_i)]$$
$$(\cos 4\phi_j \Sigma_i \cos 4\theta_i) + (\sin 2\phi_j \Sigma_i \sin 2\theta_i)$$

$$TUR_j = 2F_1F_2$$

$$DEN_j = 4[\Sigma_i(L_i/2)^2 F_{2j} - NF_{1j}]$$

and $$F1_j = \Sigma_i(L_i/2)^2 - (\cos 2\phi_j \, \Sigma_i(L_i/2)^2 \cos 2\theta_i) \\ - (\sin 2\phi_j \, \Sigma_i(L_i/2)^2 \sin 2\theta_i)$$

$$F2_j = N - (\cos 2\Phi_j \, \Sigma_i \cos 2\theta_i) - (\sin 2\Phi_j \, \Sigma_i \sin 2\theta_i)$$

Knowing the outside diameter enables a prediction of the shadow or path lengths that would be caused by a solid bar with the same outside diameter. The measured path lengths are subtracted from the solid bar path lengths and the inner circle (x, y) center and the inside diameter are determined in the same manner as the outer circle center and the outside diameter were determined, supra.

Figure 14:
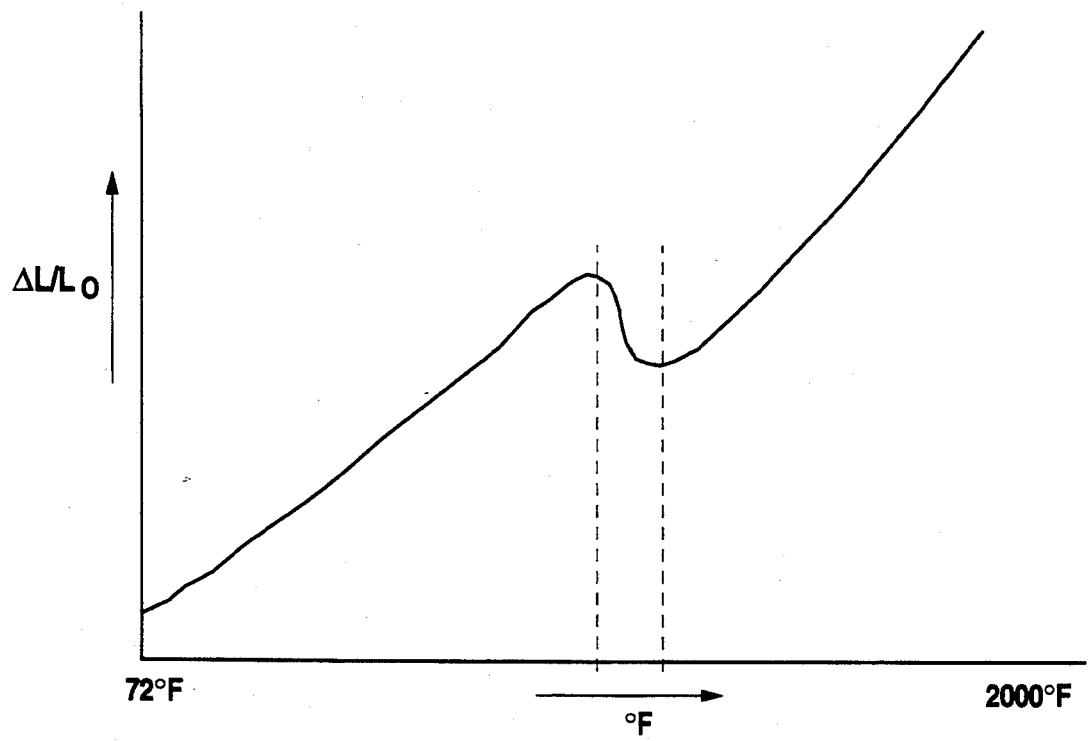
FIG. 14 is a graphic representation of a sample dilatometry curve used by the computer system to calculate ambient temperature dimensions of components inspected while at non-ambient temperatures.

In order to get more accurate data on an operating system's components dimensions, it is often necessary to measure the components while they are still hot. Unfortunately, the hot dimensions of steel pipe, for example, are not the same as the cold dimensions of the same pipe. Steel shrinks along what is commonly called a dilatometry curve, an example of which is shown in FIG. 14. Moreover, these dilatometry curves are not the same for all material compositions. For example, the percent carbon content in steel is an important factor in determining the dilatometry curve for different batches of steel. Consequently, a formula used to fit a dilatometry curve will vary depending on the material composition of the product. In the preferred embodiment of the invention, a curve fitting the dilatometry curve to obtain a formula which can be used to correct the hot temperatures is performed outside the computer system 46, the dilatometry curve fit formula for the material inspected is entered into the computer. With temperature information from the temperature sensors, more accurate temperature corrected measurements can be obtained.

After several rotational scans have been performed the computer system 68 calculates the average OD and ID for each cross-section of the pipe. These averages are needed to calculate cross-sectional ovality and eccentricity.

The ovality, which is defined by the dimensional difference between maximum and minimum outside diameter as rotated around the circumference of the pipe, is calculated after computation of the average outside diameter and inside diameter for each sectional along the length of the pipe. It is assumed that the outer surface, "S", of the pipe can be described by an average radius, "R", that is modulated by a sine function of amplitude, "A", such that:

$$S(\theta) = R + A(\sin 2\theta)$$

The ovality is then defined as 2A. Since there are multiple measurements, one for each rotational angle from which a scan was made, a chi-squared fitting technique can be applied to solve for A.

Eccentricity is determined by using the (x, y) centers previously calculated. The eccentricity is physically defined as the dimensional displacement of the center of the outer surface of the pipe from the center of the inner surface of the pipe. The average (x,y) centers for both outside diameter and inside diameter for each section along the pipe are calculated. The averages are then vectorially subtracted from each other to find the total displacement:

$$D = SQRT\,[(X_{OD} - X_{ID})^2 + (Y_{OD} - Y_{ID})^2]$$

where "($X_{OD}$, $Y_{OD}$)" is the average co-ordinate for the outer surface center, "($X_{ID}$, $Y_{ID}$)" is the average co-ordinate for the inner surface center, and "D" is the displacement between the two average center co-ordinates.

After the ovality, eccentricity and minimum wall thickness have been calculated, the computer system 68 can take the hot temperature measurements of the pipe and calculate/predict the anticipated cold temperature dimensions of the pipe. The cold dimensions of the pipe are calculated/predicted using the following formula:

$$D_c = F(D_h)$$

where "$D_c$" is the cold temperature dimension, "$D_h$" is the hot temperature dimension, and "$F(D_h)$" is the function representing the function which was form fit to the dilatometry curve of the material from which the scanned object is made and which was input into the computer system 68 by the operator.

After the calculations have been made the computer system 68 calculates the variance between the measured actual dimensions of the pipe and the desired dimensions of an ideal pipe. These variances represent flaws in the pipe. The calculations include variances in: OD, ID, wall thickness, eccentricity and ovality.

CALIBRATION

In addition to the computer programs described above, the Apparatus includes a calibration program. Calibrating the apparatus A is essential to obtaining accurate results. The calibration program for this particular embodiment performs two separate and independent calibrations: one calibration determines geometric parameters of the scanning apparatus S, and the other calibration determines the path length quadratic correction parameters for each detector 238, the use of which was described previously.

Since the preferred embodiment contains one source 58 and detector array 60 pairing, the geometry of the scanner apparatus S is defined in at least 3 parameters which are all measured from the scanning apparatus' S center: one parameter defines the distance of the source 58 from the center, one parameter define the distances of each detector array 60 from the center of the scanning apparatus S, and one parameter defines the interdetector spacing between each detector 238 in the detector array 60.

Figure 15A:
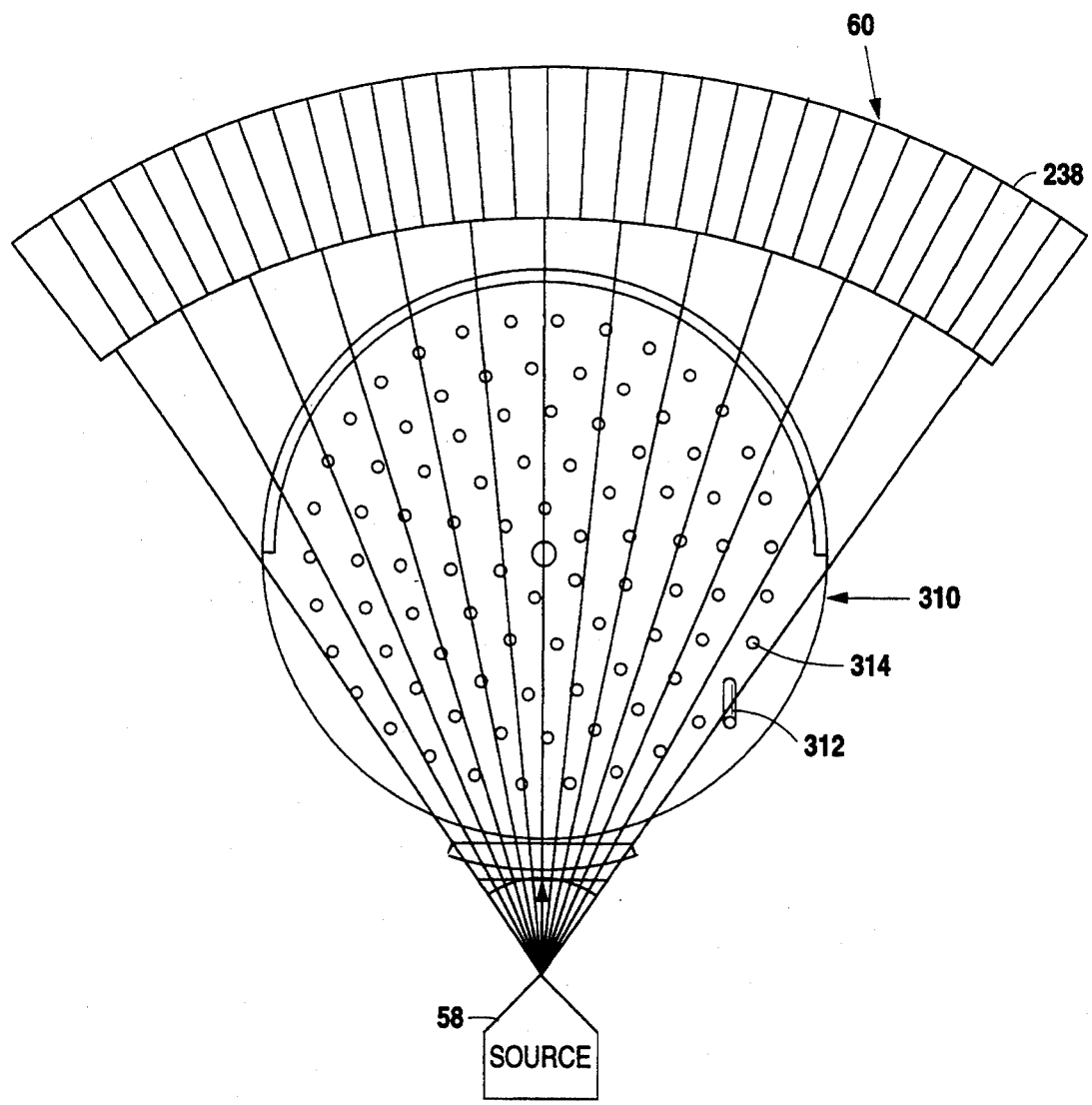
FIG. 15A is a simplified diagrammatic representation of the calibration plate in position between a source and detector array which is used to calibrate the geometrical relationship of an object.

The method used to determine these parameters involves a calibration plate 310 (FIG. 15A) which can position a steel bar 312 in a multitude of known calibrated locations 314. The preferred embodiment utilizes a calibration plate/steel bar design with 91 different calibrated locations 314. After a measurement has been taken by the apparatus for each of the locations, a chi-squared minimization is performed by the geometry parameter calibration program to determine the geometric parameters of the apparatus.

The second calibration performed by the calibration program is designed to normalize the path length calculation from one detector 238 to another in order to have consistent results as the pipe varies from the center of the scanning apparatus. This calibration is necessary because the inspection is performed in a not contacting manner and therefore the pipe is not always concentric with the center of the scanning apparatus S. The formula used to normalize the path length is the following:

$$L' = X + (Y)(L) + (Z)(L)$$

Figure 15B:
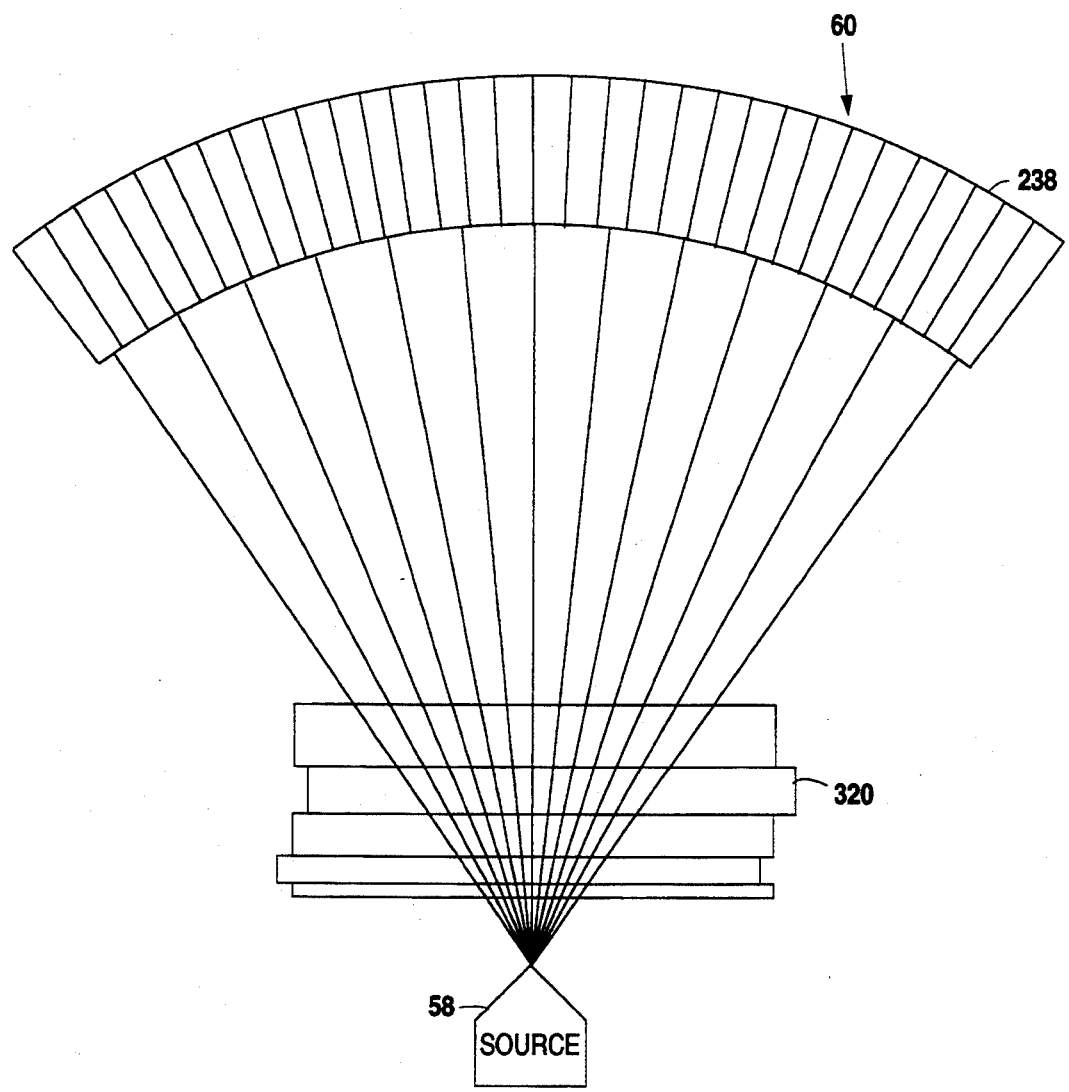
FIG. 15B is a simplified diagrammatic representation of calibration plates of varying thickness in position between a source and detector array which are used to calibrate the individual detectors of the detector array.

Each detector 238 has a unique "$X_i$", "$Y_i$", and "$Z_i$" which is calculated and determined by the calibration program. The method used to determine these parameters involves a set of steel plates 320 (FIG. 15B) that vary in thickness from 0.5 inches to 5.5 inches, in 0.5 inch increments. After unnormalized measurements are taken for each plate, a chi-squared minimization is performed to determine the normalization parameters "$X_i$", "$Y_i$", and "$Z_i$" for each detector 238. These parameters are used later where path lengths are calculated during normal operation.

ANALYTIC MODE

In the analytical mode, the computer 68 is programmed to employ conventional computer tomographic principles summarized in U.S. Pat. No. 4,284,895, except that the programming must also be adapted to an object-centered detector array system geometry as described above rather than a source-centered detector array system geometry as described above. Preferably, the computer 68 is programmed to employ a Radon-based analytic reconstruction technique, such as those based on the Fourier or Convolution reconstruction theorems, to form a first estimate of the linear attenuation coefficient of each pixel or element of the component. Then iterative reconstruction techniques can be employed to refine the estimate to obtain a final estimate of the attenuation coefficient.

Although the methods used to analyze the data collected in the analytical mode generate results with high resolution and precision, they require much more data and a great deal more time to complete. In comparison, the methods used in the gauging mode are less accurate; however, they require substantially less data and require substantially less time for completion.

Another characteristic that distinguishes the scanning modes is the type of movement required of the mechanical system. The gauging mode type scans only require that the mechanical system rotate the source 58 and detector array housing 60 to a limited number of rotational positions 346 or angles. An example of a set of rotational positions used in a gauging mode scan is shown in FIG. 16A. FIG. 16A shows 5 macro-steps 342 and 3 micro steps 340 per macro-step 342. The density of data per cross-section of the component depends on the number of macro 342 and micro 340 steps taken.

Another characteristic distinguishing the gauging mode from the analytic mode is the option to translate along a given length of the component for each rotational position 346 shown in FIG. 16A.

The use of the translational scan option is shown in FIG. 16B. This figure shows a series of translational scans for two macro-steps 342 with three micro-steps 340 each. The increasing numerals indicate the positional sequence of the source as the component is being scanned. The source 58 and detector array 242 are held in a rotationally fixed position and the ring assembly 54 is translated along the length of the component 18 taking scans at predetermined intervals. Once the ring assembly 54 has been translated the length of the component 18, it is rotated a few degrees if a macro-step is contemplated or a portion of a degree if a micro-step is contemplated and then is translated back along the same length of the component 18. After the ring assembly 54 has returned to its original position the ring assembly 54 is again rotated and translated along the length of the component 18. After a series of these small rotational scans 340, the ring assembly 54 makes a larger rotation 342,—degrees for example. The operator of the system specifies the number and size (in degrees) for macro-steps 342, micro-steps 340, the number of translational steps and the size (in units of length). The degree of resolution in the gauging mode is determined by the number and size of macro-steps 342 and micro-steps 340 steps and also the number of translational steps per unit length. The larger the number of macro 342 and micro 340 and translational steps the greater the resolution but the slower the total scan time.

Another option in the gauging mode is to take sub-positional measurements for each rotational position of the ring assembly. While micro-steps typically range from a few degrees to a fraction of a degree, sub-positioning changes the angular positions of the detector array housing 60 by a fraction of a degree to a very small fraction of a degree, 1/30 of a degree, for example. Although sub-positioning increases the data density and therefor the resolution of the results it also substantially increases the time required to collect the data.

In the analytical mode the large number of rotational positions of the ring assembly 54 around the component scanned blurs the distinction between macro-steps 342 and micro-steps 340, rather there are simply a large number of micro steps 340 for each cross-section of the component 18 scanned by using an analytical mode.

The analytical mode also allows the option of using sub-positioning for each rotational position to increase the data density of the scan. However, unlike the gauging mode in the analytical mode, the scanning apparatus S does not typically translate longitudinally along the length of the component 18 for each rotational position 346 as shown in FIG. 16B. Rather in the analytical mode since localized cross-sections are the focus of the scan, the scans for one cross-section are completed before beginning a new cross-section.

Prior to scanning the component 18 the operator of the system inputs the scanning mode parameters. If a gauging mode scan is desired the operator must define the number of macro-steps 342, additionally if the operator wishes to define the scanning mode to include micro-steps, sub-positioning and or translational movement these parameters must also be entered. On the other hand, if an analytical mode scan is desired, the operator must define the number of rotational positions for each cross-section and the number of sub-positions per rotational position if any.

In the preferred embodiment of this invention the operator has the option and flexibility to define a number of scanning modes and use them separately or together to inspect a component 18. An example of using several differently defined scanning modes to scan a section of pipe in a steam power generating facility is described in the operation below.

OPERATION

In a steam power generating facility environment shown in FIG. 2, the present invention is implemented by positioning the beam 80 of the gantry assembly 52 in parallel with the axis of the component 18 to be examined. The gantry 52 should be at a distance from the component 18 to be scanned so that when the ring assembly 54 is closed about the component 18, the center of the component 18 and the center of the ring assembly 52 are approximately concentric. The invention is now capable of traveling along the length of the component 18 and rotating about the component 18 through the gantry 52, yoke 84 and ring assembly 54 means described above. As the invention moves, it can scan cross-sections of the component 18 with penetrating radiation through use of the source 58 and detector array 242 described above.

Figure 17:
FIG. 17 is an illustrative drawing of a dimensional gauge scanning mode's longitudinal scan results of a pipe's outside diameter inside diameter and wall thickness.

The description of a preferred operation of the present invention uses several differently defined scanning modes depending on the type of flaws detected. The first scanning mode is a gauging mode scan with typically seven macro-steps 342, one micro-step 340 per macro-step 342, no sub-positioning, and longitudinal coverage of 10 feet of pipe. The scanning apparatus S quickly scans the length of the pipe 18 at one rotational position then rotates a micro-step 340 and travels back along the same length of pipe. The scanning apparatus S then takes a macro-step 342 and again travels the length of the pipe 18. This process repeats itself until the all of the rotational steps 342 & 340 have been taken and the entire length of the pipe is scanned for each rotational position 346. This scanning mode is called the dimensional gauge scanning mode since as it travels along the length of the pipe it can use the limited angle data collection and analysis techniques disclosed in U.S. Pat. No. 4,725,963, to Taylor, et al., entitled "Method and Apparatus for Dimensional Analysis and Flaw Detection of Continuously Produced Tubular Objects" and PCT Publication No. PCT/US91/03828 entitled "An Automated system for Controlling the Quality of Geometrically Regular Shaped Products during Their Manufacture," to calculate the pipe's inside diameter, outside diameter and wall thickness. After the scan is complete, the computer 68 calculates eccentricity, and ovality using the limited angle data analysis techniques disclosed in PCT Publication No. PCT/US91/03828 the description of which is incorporated herein. The outputs from this part of the dimensional gauge scanning mode analysis can be graphically displayed as shown in FIG. 17.

Figure 18A:
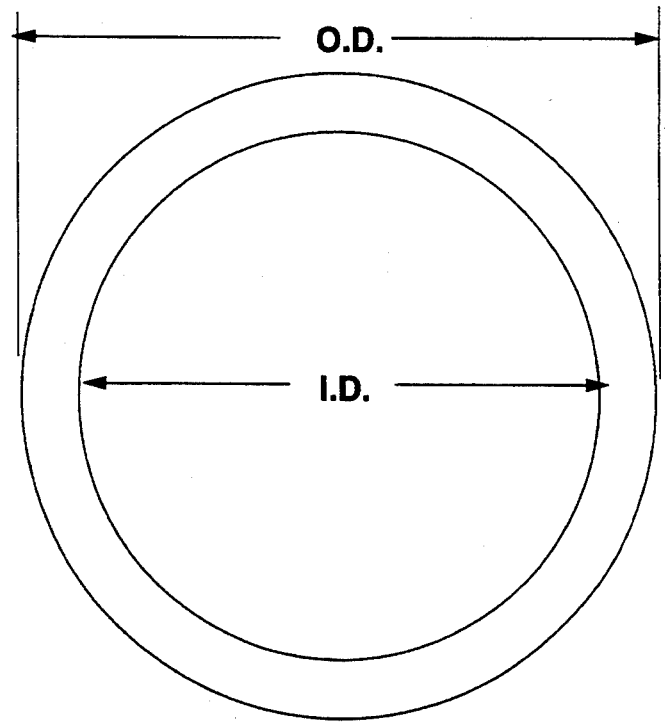
FIGS. 18A and B are illustrative drawings of a model pipe profile based on average data of outside diameter, inside diameter and wall thickness.
Figure 18B:
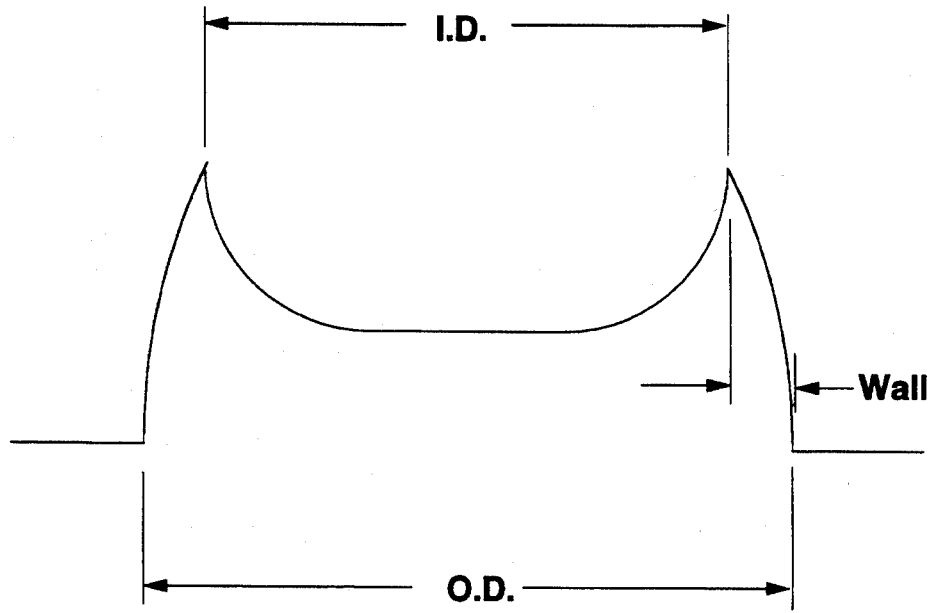
Figure 19A:
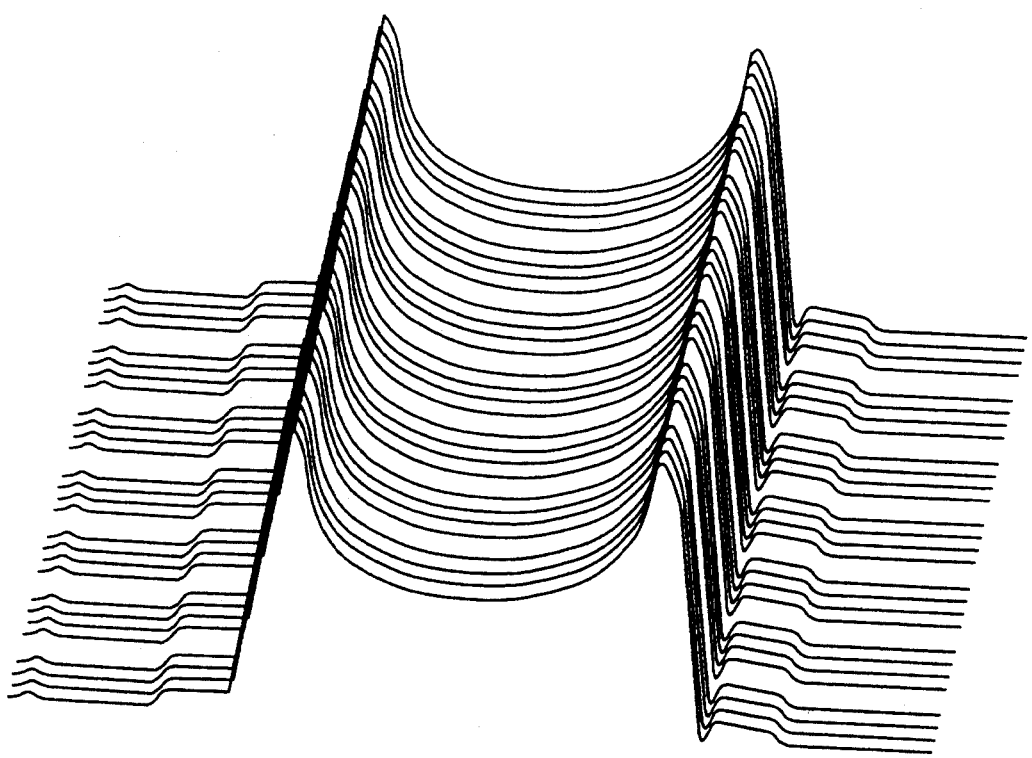
FIG. 19A is an illustrative waterfall display drawing of actual measured pipe profiles.
Figure 19B:
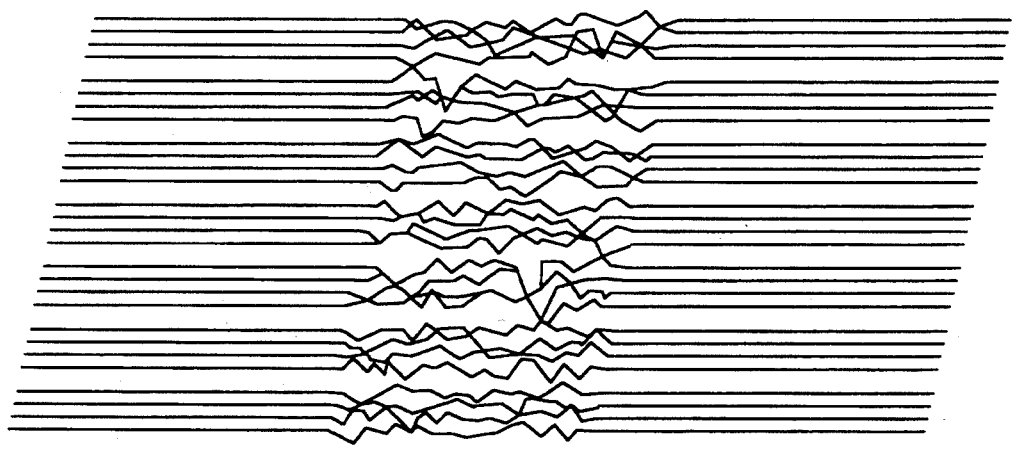
FIG. 19B is an illustrative waterfall display drawing of the difference resulting from subtracting the model pipe profile in FIG. 18B from each profile in FIG. 19A.

The computer 68 then calculates an overall average OD, ID, and wall thickness. This information is used to generate a computer model of an ideal section of the pipe scanned. FIG. 18B is an illustration of the computer profile model of an ideal section of pipe as determined by the pipe averages calculated above. The computer 68 then subtracts the calculated ideal model profile from the actually measured profiles. The difference is a representation of how each profile deviates from ideal. FIG. 19A illustrates a series of actual pipe profiles from a dimensional gauge scanning mode as described above. FIG. 19B illustrates the results when the ideal pipe profile model is subtracted from the actual profile. If these deviations exceed a threshold previously set by the operator, the computer 68 will store the associated longitudinal and angular positions and identify the deviation as a particular class of anomaly. If the anomaly is a narrower wall thickness, then wall thinning is identified as the type of flaw. If the OD is larger than average, then creep is identified as the flaw. If the OD is only larger on a portion of the outer surface of the pipe, then plastic deformation is identified as the type of flaw. If the anomaly is small and localized, its longitudinal position along the length of the pipe is marked for further investigation. The computer 68 is also able to identify weld locations, plugs and attachments beneath the insulation because of their unique effects on the component profile at various angular views.

After the computer 68 has completed the above described calculations, the apparatus begins a higher resolution gauge scanning mode in longitudinal positions where anomalies were identified by the dimensional gauge scanning mode. In this scanning mode, the apparatus typically scans the localized area at 15 macro-step locations 342 and 8 micro-steps 340 per macro-step 342, 360 degrees about the component. No sub-positioning is called for and the longitudinal length of each scan is determined by the results of the dimensional gauge scanning mode. The scanning sequence is essentially the same as was previously described in the dimensional gauge scanning mode description except for the increased number of scans.

As its name indicates the higher resolution gauge scanning mode generates higher data densities sufficient to make more accurate measurements of the dimensions determined in the dimensional gauge scanning mode and also more accurately analyze the magnitude and location of the anomalies.

Figure 20:
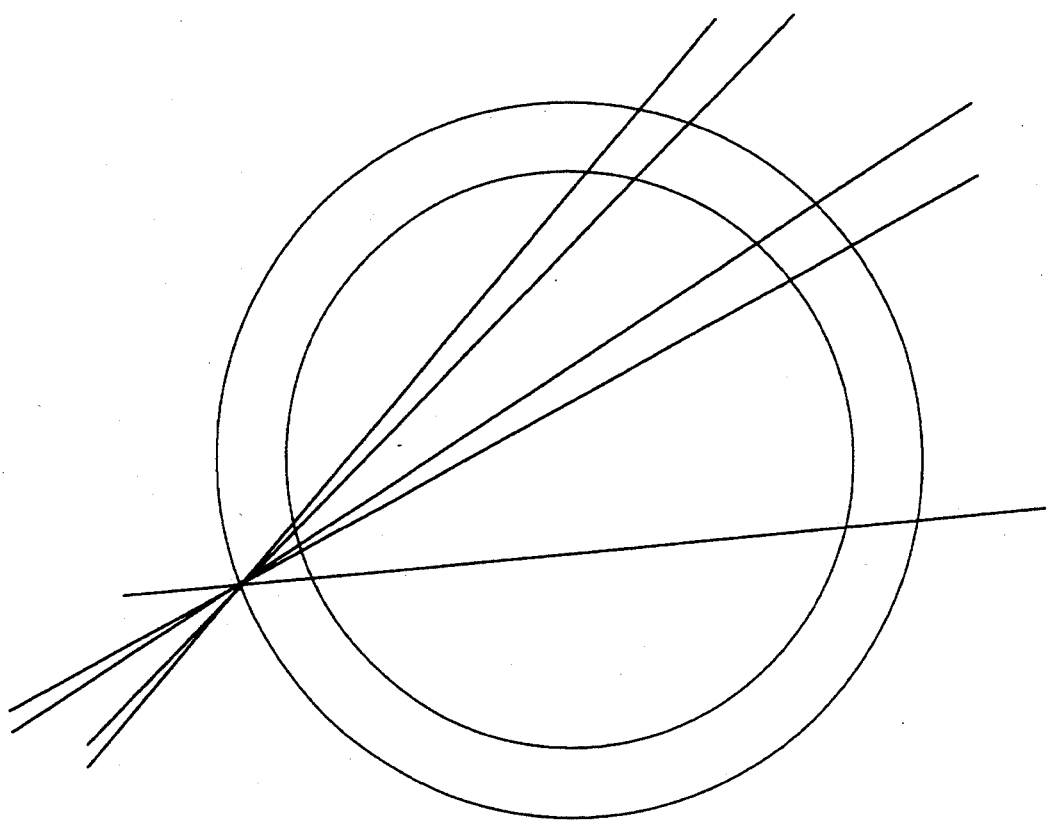
FIG. 20 is an illustrative drawing of how density length paths can be used to triangulate on the location of an anomaly.

The location of flaws can also be determined by the computer 68 from data taken in a high resolution gauge mode by triangulation. As shown in FIG. 20, triangulation is performed by calculating the intersection of all the path lengths in which the flaw was detected.

The type of flaw (corrosion wear, erosion wear, pitting, cavitation, gouges, voids, and cracks) can be identified by the shape by comparison to the flaw shape previously determined to empirical shape characteristics of typical flaws.

If a weld or crack or any other anomaly for which more detailed information would be useful was identified in either of the gauging mode scans, the apparatus may be moved to the longitudinal location of these anomalies to perform a low resolution analytical mode scan. The low resolution analytical mode scan typically has approximately 360 degree rotational positions and one sub-position for each rotational position. In the analytical mode one cross-section of the component is typically completely scanned before being longitudinally translating to a second cross-section.

Once the low resolution analytical mode scan is complete the computer 68 utilizes conventional tomographic algorithms as described above to generate a three dimensional tomographic image of the flaw. These high resolution results allow for the characterization of anomalies not inspectable by the apparatus during the gauge modes, for example, smaller lugs, attachments, plugs, cracks indications and welds where a resolution of greater than 0.5% is needed. In the case of welds or other areas where the density of the component is not consistent, the scan can be run twice, once with each source 202 & 204. The path-lengths from these two scans can be used to calculate the density of the component using available algorithms.

If the detail obtained from the low resolution analytical mode scan is not enough, a high resolution analytical mode scan can be run. Typically, the scanning apparatus during a high resolution scan made will move to 1080 rotational positions and S sub-positions per rotational position. Using the data collected in this scan, the computer 68 utilizes the same CT algorithms described above.

The foregoing disclosure and description of the invention are illustrative and explanatory thereof, and various changes in the details of its construction or mode of operation of the inspection and analysis may be made without departing from the spirit of the invention.

We claim:

1. A mobile apparatus for nondestructively scanning stationary insulated cylindrically shaded components of a facility while the facility is in operation, without removing the insulation from the component under examination, comprising:
   a) means for transmitting penetrating radiation along a plurality of paths through a full cross-section of the insulated component;
   b) detector means for detecting penetrating radiation which passes through the component from said transmitting means and for converting the detected radiation into electrical signals representative of the density length of the component material along a path between said transmitting means and said detector means;
   c) ring means, for encircling the insulated component to be scanned on which said transmitting means and detector means are mounted, wherein the ring means includes:
      i.) an outer ring having at least two sections,
      ii) inner ring having of at least two sections,
      iii) a plurality of recirculating tracks positioned so that the inner or outer ring can be rotated relative to the other, and
      iv) means for aligning the inner and outer rim, sections to allow the ring means to be opened and closed about the component to be scanned;
   d) means, positioned along a length of the component, for supporting said ring means wherein said supporting means and ring means are in a non-contacting relationship with the section of the component scanned;
   e) means for rotating the ring means relative to said support means about a cross-section of the component to be scanned in such a manner that the penetrating radiation paths remain in the same cross-sectional plane for each cross-section scanned;
   f) means for translating the ring means relative to the support means along the length of the component to be scanned without causing the ring means to contact the component;
   g) means for monitoring the longitudinal position of the ring means relative to the support means; and
   h) means for monitoring the rotational position of the ring means relative to said support means.

2. The apparatus of claim 1, further comprising:
processing means for receiving positional data from the monitoring means, for sending control signals to the translating and rotating means for translating and rotating the transmitting means and detector means, and for receiving density length signals from the detector means for each of a plurality of translated and rotational positions.

3. The apparatus of claim 2, wherein:
   a) said processing means further comprises a computer model for performing a gauging analysis of the component scanned; and
   b) The processing means processes the density length signals and positional data using the computer model in order to detect flaws in the component scanned and the location of the flaw in the component.

4. The apparatus of claim 3, wherein:
the computer model of the component is generated by said processing means from density length signals generated by the apparatus scanning the component at a plurality of longitudinal and rotational positions during a gauging mode.

5. The apparatus of claim 3, which further comprises:
   a) stored data representative of a profile of a plurality of cross-sections of the component scanned; and
   b) said processing means compares the representative and real profiles of the component to find differences representative of flaws in the component scanned.

6. The apparatus of claim 5, which further comprises:
program means for generating a plurality of control signals for operating the apparatus during a high resolution gauging mode wherein, during such high resolution gauging mode, the apparatus rescans at least the portion of the component having a detected flaw from a larger number of longitudinal and rotational positions than the positions scanned in the gauging mode in order to more accurately determine the dimensions and characteristics of the flaw in order to correlate such dimensions and characteristics to phenomena historically producing similar flaw dimensions and characteristics.

7. The apparatus of claim 5, which further comprises:
program means for operating the apparatus during an analytical mode wherein the apparatus scans at least a portion of the component containing a previously detected flaw from many rotational positions about the component and uses the resulting signals to generate a tomographic reconstruction of the portion of the component containing the previously detected flaw.

8. The apparatus of claim 3, further comprising:
   a) means for measuring the temperature of the component scanned; and
   b) means for adjusting the computer model of the scanned component to account for variations in temperature.

9. A method of nondestructively inspecting components of an operating facility while the components are in use, comprising:
   a) positioning a penetrating radiation scanning apparatus having a source and a detector about the component to be scanned;
   b) scanning a cross-section of the component with penetrating radiation along a plurality of planar paths;
   c) generating signals representative of the radiation attenuation along each of a plurality of paths;
   d) converting the attenuation signals to density length signals and storing the density length signals in a computer memory;
   e) monitoring the longitudinal and rotational position associated with the density length signals generated by the scan, generating signals representative of the longitudinal and rotational position, and storing the signals in a computer memory;
   f) translating the scanning apparatus to another longitudinal position along the component;
   g) repeating steps (b) through (f) until a length of the component has been scanned;
   h) rotating the scanning apparatus about the axis of the component;
   i) repeating steps (b) through (f) until a length of the component has been scanned;

j) processing the density length signals from the plurality of scans using a computer model of the cross-section of the component in order to calculate the dimensions of different cross-sections of the component and/or detect flaws in the component; and k) processing the density length and position signals to determine the location of any detected flaws by triangulation.

* * * * *